(12) United States Patent
Mohr et al.

(10) Patent No.: US 8,445,675 B2
(45) Date of Patent: May 21, 2013

(54) STORAGE STABLE PERFUSION SOLUTION FOR DIHYDROPTERIDINONES

(75) Inventors: Detlef Mohr, Biberach (DE); Claus Veit, Biberach (DE); Fridtjof Traulsen, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 328 days.

(21) Appl. No.: 12/366,730

(22) Filed: Feb. 6, 2009

(65) Prior Publication Data
US 2009/0143379 A1 Jun. 4, 2009

Related U.S. Application Data

(63) Continuation of application No. 11/197,927, filed on Aug. 5, 2005, now abandoned.

(30) Foreign Application Priority Data

Aug. 14, 2004 (DE) ................................ 040 19 363

(51) Int. Cl.
*C07D 417/00* (2006.01)
*C07D 413/00* (2006.01)
*C70D 237/00* (2006.01)

(52) U.S. Cl.
USPC ............. 544/61; 544/118; 544/231; 544/251; 544/257; 544/258

(58) Field of Classification Search
USPC ........................................... 544/61, 118, 231
See application file for complete search history.

(56) References Cited

U.S. PATENT DOCUMENTS

| | | | |
|---|---|---|---|
| 4,870,175 A | 9/1989 | Suzuki et al. | |
| 4,957,922 A | 9/1990 | Lammens et al. | |
| 5,167,949 A | 12/1992 | Ferrand et al. | |
| 5,198,547 A | 3/1993 | Bailey et al. | |
| 5,424,311 A | 6/1995 | Billhardt-Troughton et al. | |
| 5,698,556 A | 12/1997 | Chan | |
| 6,096,924 A | 8/2000 | Studer et al. | |
| 6,156,766 A | 12/2000 | Arita et al. | |
| 6,174,895 B1 | 1/2001 | Kleinman | |
| 6,605,255 B2 | 8/2003 | Kroll et al. | |
| 6,806,272 B2 * | 10/2004 | Bauer et al. | 514/250 |
| 6,861,422 B2 | 3/2005 | Hoffmann et al. | |
| 6,875,868 B2 | 4/2005 | Bonnert et al. | |
| 7,238,685 B2 | 7/2007 | Duran et al. | |
| 7,241,889 B2 | 7/2007 | Hoffmann et al. | |
| 7,332,491 B2 | 2/2008 | Grauert et al. | |
| 7,371,753 B2 | 5/2008 | Stadtmueller et al. | |
| 7,414,053 B2 | 8/2008 | Grauert et al. | |
| 7,439,358 B2 | 10/2008 | Linz et al. | |
| 7,547,780 B2 | 6/2009 | Grauert et al. | |
| 7,625,899 B2 | 12/2009 | Hoffmann et al. | |
| 7,626,019 B2 | 12/2009 | Duran et al. | |
| 7,629,460 B2 | 12/2009 | Grauert et al. | |
| 7,700,769 B2 | 4/2010 | Grauert et al. | |
| 7,723,517 B2 | 5/2010 | Grauert et al. | |
| 7,728,134 B2 | 6/2010 | Linz et al. | |
| 7,750,152 B2 | 7/2010 | Hoffman et al. | |
| 7,759,347 B2 | 7/2010 | Hoffmann | |
| 7,759,485 B2 | 7/2010 | Linz et al. | |
| 7,807,831 B2 | 10/2010 | Grauert et al. | |
| 7,816,530 B2 | 10/2010 | Grauert | |
| 8,003,786 B2 | 8/2011 | Hoffmann et al. | |
| 8,034,816 B2 | 10/2011 | Linz et al. | |
| 8,058,270 B2 | 11/2011 | Munzert et al. | |
| 8,138,341 B2 | 3/2012 | Linz et al. | |
| 8,138,373 B2 | 3/2012 | Linz et al. | |

(Continued)

FOREIGN PATENT DOCUMENTS

| | | |
|---|---|---|
| CA | 2458699 A1 | 3/2003 |
| CA | 2517020 A1 | 10/2004 |

(Continued)

OTHER PUBLICATIONS

Eurasian Patent Office, Maly Zlatoustinsky per., d. 10, kv. 15, 101000 Moscow Russia, "EVROMARKPAT", Opinion, Re.No. 94187, Mar. 1, 2007.

(Continued)

*Primary Examiner* — Shirley V Gembeh
(74) *Attorney, Agent, or Firm* — Michael P. Morris; Anthony P. Bottino

(57) ABSTRACT

Disclosed are storage stable aqueous infusible or injectable solutions containing an active substance of general formula (I)

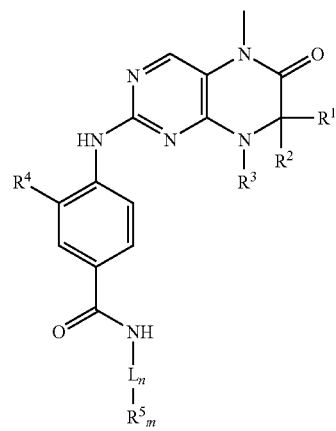

wherein the groups L, $R^1$, $R^2$, $R^3$, $R^4$ and $R^5$ have the meanings given in the claims and in the specification, and an amount of a physiologically acceptable acid or mixture of acids sufficient to dissolve the active substance and act as a stabilizer, optionally together with other formulating excipients suitable for parenteral administration, and a process for preparing the infusible or injectable solutions according to the invention.

18 Claims, 1 Drawing Sheet

U.S. PATENT DOCUMENTS

| | | | |
|---|---|---|---|
| 8,143,247 B2 | 3/2012 | Munzert et al. |
| 8,188,086 B2 | 5/2012 | Linz et al. |
| 8,193,188 B2 | 6/2012 | Hoffmann et al. |
| 8,202,867 B2 | 6/2012 | Linz et al. |
| 8,329,695 B2 | 12/2012 | Linz et al. |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2004/0024205 A1 | 2/2004 | Borredon et al. |
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0029642 A1 | 2/2010 | Hoffmann et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |
| 2012/0107312 A1 | 5/2012 | Munzert et al. |
| 2012/0214995 A1 | 8/2012 | Linz et al. |
| 2012/0238754 A1 | 9/2012 | Schnaubelt et al. |
| 2012/0295864 A1 | 11/2012 | Taube et al. |
| 2012/0296091 A1 | 11/2012 | Sieger et al. |

FOREIGN PATENT DOCUMENTS

| | | | |
|---|---|---|---|
| CA | 2517010 A1 | 11/2004 |
| CA | 2576290 A1 | 2/2006 |
| EP | 0143478 A1 | 5/1985 |
| EP | 347146 A2 | 12/1989 |
| EP | 399856 A1 | 11/1990 |
| EP | 0429149 A1 | 5/1991 |
| ES | 2287583 | 12/2007 |
| JP | 2009169737 A | 6/1997 |
| RU | 2002125451 A | 1/2004 |
| WO | 9608537 A1 | 3/1996 |
| WO | 9609045 A1 | 3/1996 |
| WO | 9634867 A1 | 11/1996 |
| WO | 9636597 A1 | 11/1996 |
| WO | 9811893 A1 | 3/1998 |
| WO | 0119825 A1 | 3/2001 |
| WO | 0170741 A1 | 9/2001 |
| WO | 0178732 A1 | 10/2001 |
| WO | 02057261 A2 | 7/2002 |
| WO | 02076954 A1 | 10/2002 |
| WO | 02076985 A | 10/2002 |
| WO | 03020722 A1 | 3/2003 |
| WO | 03093249 A1 | 11/2003 |
| WO | 2004014899 A1 | 2/2004 |
| WO | 2004076454 A1 | 9/2004 |
| WO | 2004093848 A2 | 11/2004 |
| WO | 2005067935 A1 | 7/2005 |
| WO | 2006005510 A1 | 1/2006 |
| WO | 2006/018182 A1 | 2/2006 |
| WO | 2006/018221 A1 | 2/2006 |
| WO | 2006018185 A2 | 2/2006 |
| WO | 2006018220 A2 | 2/2006 |
| WO | 2006018221 A1 | 2/2006 |
| WO | 2006021378 A1 | 3/2006 |
| WO | 2006021379 A1 | 3/2006 |
| WO | 2006021547 A1 | 3/2006 |
| WO | 2007054551 A1 | 5/2007 |
| WO | 2007090844 A1 | 8/2007 |
| WO | 2009019205 A1 | 2/2009 |
| WO | 2009112524 A1 | 9/2009 |
| WO | 2011101369 A1 | 8/2011 |
| WO | 2012049153 A1 | 4/2012 |
| WO | 2012156283 A1 | 11/2012 |
| WO | 2012156380 A1 | 11/2012 |

OTHER PUBLICATIONS

Masuda, et al., Oncogene (2003) 22, 1012-1023.
Ito, et al., "Polo-like kinase 1 (PLK1) expression is associated with cell proliferative activity and cdc2 expression in malignant lymphoma of the thyroid" Anticancer Research, 2004, vol. 24, No. 1, pp. 259-263 (hhttp://cat.inist.fr/?aModele=afficheN &cpsidt=15622521 Nov. 17, 2006—Abstract).
Mito, et al., "Expression of Polo-Like Kinase (PLK1) in non-Hodgkin's lymphomas," Leuk. Lymphoma, Feb. 2005, 46(2): 225-31 (PubMed abstract).
Verschuren, et al., "The cell cycle and how it is steered by Kaposi's sarcoma-associated herpesvirus cyclin" J. Gen. Virology (2004), 85, pp. 1347-1361.
Tor Ahlenius, Listing of cardiovascular disorders/diseases, Karolinska Instiutet Library, Stockholm, Sweden, http://www.mic.ki.se/diseases/c14.html, pp. 1-34, Apr. 2007.
Wolf, Donald E., et al., "The Structure of Rhizopterin", J. Am. Chem. Soc., vol. 69, pp. 2753-2759, 1947.
Ferrand, G. et al: "Synthesis and potential antiallergic activity of new pteridinones and related compounds." European Journal of Medicinal Chemistry, Vo. 31, #4, 1996, pp. 273-280.
Kimball, S.D., et al; Ann. Reports Med. Chem., vol. 36, 2001, pp. 139-148.
Savelli, F.& Boido, A;. "Heterocyclic System Part II-Synthesis of New Pyrido [1'2':4,5] pyrazino [3,2-d] pyrimidines"; Bollettino Chimico Farmaceutico, 131(8), 309-12, Sep. 1992.
Katherine Arnold, "Collaboration to Play Key Role in NCI's Future, Director Says" Journal of the National Cancer Institute, Jun. 5, 2002, pp. 790-792, vol. 94, No. 11. Http://jncicancerspectrum.oxfordjournals.org/cgi/content/full/jnci;94/11/790.
The Merck Manual of Medical Information—Home Edition, Section 17, Parasitic Infections, Chapter 184 on the web site http://www.merck.com/mrkshared/mmanual_home/sec17/184.jsp, downloaded on Nov. 26, 2003.
International Search Report, Reference No. PCT/EP2005/008990, 2005.
N. Takai, et al., "Polo-like (Plks) and cancer". Oncogene, 2005, 24, pp. 287-291.
Karolinksa Institute. Cardiovascular Diseases, pp. 1-34.
ACPS Meeting, Background Information. "Scientific considerations of plymorphism in pharmaceutical solids: abbreviated new drug applications". Oct. 2002.

Ahmad, N. "Polo-like kinase (Plk) 1: a novel target for the treatment of prostate cancer". Dept of Dermatology, Univ. Wisconsin, pp. 3-5. FASEB J. 18, 5-7 (2004).

BBC News/Health, Killer Breast Cancern Therapy Hope, www.newsvote.bbc/co./uk, downloaded Mar. 26, 2009.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Dipolar aprotic solvent. Exhibit A, IUPAC Compendium of Chemical Terminology, 2nd Edition, 1997.

Doerwald, F.Z. "Side reactions in organice synthesis". 2005.

Ghandi, L., et al., "An Open-Label Phase II Trial of the PLK Inhibitor BI 2536 in Patients with Sensitive Relapse Small Cell Lung Cancer". ASCO Meeting 2009.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

Jaworska, J., et al., "Review of methods for assessing the applicability domains of SARS and QSARS". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

Leukemia & Lymphoma Society—Disease Information-Lymphoma. www.leukemia-lymphoma.org/all_page?item_id-7030, downloaded Mar. 26, 2009.

Leukemia & Lymphoma Society—Disease Information. www.leukemia-lymphoma.org/all_page?item_id-7026, downloaded Mar. 26, 2009.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

MedlinePlus: Bacterial Infections. www.nim.nih.gov/medlineplus/print/bacterialinfections.htm, downloaded Mar. 26, 2009.

MedlinePlus: Viral Infections. www.nim.nih.gov/medlineplus/print/viralinfections.htm, downloaded Mar. 26, 2009.

Nagao, K. et al., "Effect of MX-68 on airway inflammation and hyperresponsiveness in mice and guinea-pigs". Journal of Pharmacy and Pharmacology, JPP 2004, 56, pp. 187-196.

National Institute of Neurological Disorders, Index Stroke, 2006.

National Kidney Foundation: Chronic Kidney Disease (CKD). www.kidney.org/kidneydisease/ckd/index.cfm, downloaded Mar. 26, 2009.

Norman, P. "PDE4 inhibitors". 1999, Ashley Publications Ltd., pp. 1101-1118.

Office Action mailed Dec. 10, 2003 for U.S. Appl. No. 10/226,710, filed Aug. 23, 2002.

Office Action mailed Apr. 28, 2004 for U.S. Appl. No. 10/374,876, filed Feb. 26, 2003.

Ohio Dept of Health, "Brain and Other Central Nervous System Cancer in Ohio, 1997-2001". Sep. 2004, pp. 1-4.

Organic Chemistry, Grupo Editorial Iberoamerica, Section 13, 3, pp. 301-302, 1983 (best copy available in Spanish).

Rylander, P.N. "Hydrgenation Methods". 1985, Chapter 13.

Rylander, P.N. "Hydrgenation Methods". 1985, Chapters 3, 4.

Rylander, P.N. "Hydrgenation Methods". 1985, Chapters 8, 9, 10, 11.

Rylander, P.N. "Hydrgenation Methods". 1985, Chapter 5, 6, 7.

Rylander, P.N., "Hydrogenation Methods". 1985, Chapters 1, 2.

Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.

Snyder, J. S. et al., "Common bacteria whose susceptibility to antimicrobials is no longer predictable". NCBI, PubMed, 2000, J. Med. Liban, 48, pp. 208-214.

Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.

Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.

Turner, W.W.et al., "Recent advances in the medicinal chemistry of antifungal agents". Current Pharmacutical Design, 1996, 2, pp. 209-224.

Vippagunta, S. R. et al., "Crystalline solids". Advanced Drug Delivery Reviews, 48, 2001, pp. 3-26.

Viral Defense Foundation. www.viraldefense.org/mission.htm, downloaded Mar. 26, 2009.

Visiting Nurse Association of America. www.vnaa.org/gen/Germ_Protection_Center_Cold_and_Flu_Resources,html, downloaded Mar. 26, 2009.

Voskoglou-Nomikos, T. et al., "Clinical predictive value of the in vitro cell line, human xenograft, and mouse allograft preclinical cancer models". Clinical Cancer Research vol. 9, 2003, pp. 4227-4239.

Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, pp. 659-668, J. Biochemical Pharmacology 63 (2002) 659-668.

Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, 19923, vol. 7, pp. 514-518.

Webster's Comprehensive Dictionary, 1996, pp. 1013-1014.

Wikipedia. "Melting Point", Jan. 17, 2007.

Chen, J.X. et al., "Parallel differentiated recognition of ketones and acetals". Angewandte Chemie Int. Ed, vol. 37, Issue 1/2, p. 91-93, 1998.

Dyson, G, et al. "The Chemistry of Synthetic Drugs". Mir 1964, p. 12-19.

Jamieson, C. et al., "Application of ReactArray Robotics and Design of Experiments Techniques in Optimisation of Supported Reagent Chemistry". Org. Proc. Res. & Dev., 2002, 6, p. 823-825.

Mashkovkii, M.D., "Medicaments". Moscow, Novaja Volna, 2001, vol. 1, p. 11.

Mashkovskii, M.D. "Drugs", Handbook for Doctors, 1993, Part I, Ch.1, p. 8.

Mayer, SF, et al., "Enzyme-initiated domino (cascase) reactions". Chem. Soc. Rev, 2001, p. 332-339.

McInnes, C. "Inhibitors of polo-like kinase reveal roles in spindle-pole maintenance". Nature Chemical Biology, vol. 2, No. 11, Nov. 2006, p. 608.

Mikhailov, I.B., Principles of Rational Pharmacotherapy. Handbook for clinical pharmacology for students of pediatric and medical faculties of medical high schools, St. Petersburg, Russia, "Foliant", 1999, p. 25.

Neidle, S. ed., "Cancer Drug Design and Discovery", Elsevier/Academic Press, 2008, p. 427-431.

Rocha Lima, C.M. et al. "Randomized phase II trial of gemcitabine plus irinotecan or docetaxel uin stage IIIB or stage IV NSCLC" Annals of Oncology, 15(3), p. 410-418, 2004.

Science, vol. 310, Oct. 21, 2005, p. 409, Chemistry: One After Another.

Souillac, P. et al., "Characterization of delivery systems, differential scanning calorimetry". (In Encyclopedia of Controlled Drug Delivery), 1999, John Wiley & Sons, pp. 212-227.

Steegmaier, M. et al. "BI 2536, a potent and selective inhibitor of polo-like kinase 1, inhibits tumor growth in vivo". Current Biology, 2007, 17(4), p. 316-322.

Stephenson, D.T. et al. "The effects of a selective dopamine D2 receptor agonist on behavioral and pathological outcome in 1-methl-4-phenyl-1,2,3,6-tetrahydropyridine-treated squirrel monkeys". J. Pharmacology and Experimental Therapeutics, vol. 303, No. 2, 2002, p. 1257.

Turner, S., "The Design of Organic Syntheses". Elsevier, 1976, pp. 10 and 149.

Walsh, F. "No "Magic Bullet" Cure for Cancer". BBC News Feb. 1, 2007, http://news.bbc,co.uk/2/health/6310697.stm, downloaded Jul. 6, 2010.

Beshore, D.C.et al., "Preparation of Substituted Piperazinones via Tandem Reductive Amination-N.N-Acyl Transfer)-Cyclization". Organic Letters, 2002, vol. 4, No. 7, p. 1201-1204.

Bug, G. et al., "Phase I/II Study of BI6727 (volasertib), An Intravenous Polo-Like Kinase-1 (PIk1) Inhibitor, in Patients with Acute Myeloid Leukemia (AML): Results of the Dose Finding for BI 6727 in Combination with Low-dose Cytarabine". Blood, vol. 116, No. 21, Nov. 19, 2010, p. 1359, American Socieity of Hematology (ASH); Orlando, FL, Dec. 2010.

Clinical Trials: NCT01348347. BI6727 (Volasertib) Monotherapy Phase I Trial in Japanese Patients with Advanced Soliid Tumours. Apr. 29, 2011 [Retrieved from the Internet: URL: http://www.clinicaltrials.gov./ct2/show/NCT01348347?term=volasertib&rank=1] retrieved Jul. 16, 2012.

Rudolph, D. et al., "430 Poster Characterization of BI 6727, a novel Polo-like kinase inhibitor with a distinct pharmacokinetic profile and efficacy in a model of taxane-resistant colon cancer". European Journal of Cancer. Supplement, Pergamon, Oxford, GB, vol. 6, No. 12, Oct. 1, 2008, p. 135. [retrieved on Oct. 1, 2008].

Schoffski, P., "Polo-like kinase (PLK) inhibitors in preclinical and early clinical development in oncology", The Oncologist, vol. 14, 2009, pp. 559-570.

Schoffski, P., et al., "A phase I single dose escalation study of the novel polo-like kinase 1 inhibitor BI 6727 in patients with advanced solid tumours", EJC Supplement, vol. 6. No. 12, Oct. 2008, p. 14-15.

Abstract in English for JP09169737, Date of Publication: Jun. 30, 1997, Applicant Tosoh Corp, Inventor: K. Hiroyuki, Title: Production of N-Methylimidazoles. Date filed: Dec. 21, 1995.

X-ray Diffraction—Factors that affect d's and I's. [Downloaded from the internet Mar. 9, 2011, URL: http://www.gly.uga.edu/Schroeder/geoI6550/XRD.html].

Gould, P. L., "Salt selection for basic drugs", International Journal of Pharmaceutics, 33(1986), 201-217.

Neau, S. H., Pharmaceutical Salts, CRC Press, 2008, Ch 17, p. 417-435.

Bastin, R. J. et al., "Salt Selection and Optimisation Procedures for Pharmaceutical New Chemical Entities", Organic Process Research and Development, 2000, 4,427-435.

Morris, K.R. et al., "An integrated approach to the selection of optimal salt form for a new drug candidate", International Journal of Pharmaceutics, 105, 1994, 209-217.

Badawy, S. I. et al., "Sale Selection for Phamaceutical Compounds", Preformulation in Solid Dosage Form Develolpment, Infoa Healthcare 2008, Chapter 2.3, 63-80.

Serajuddin, Abu T.M., "Salt formation to improve durg solubility", Advanced Drug Delivery Reviews, 59, 2007, 603-616.

"Salt Forms of Drug Absorption", Swarbrick, et al. editors, Encyclopedia of Pharm. Tech. 13 Marcel Dekker, NY, 1996, 453-499.

\* cited by examiner

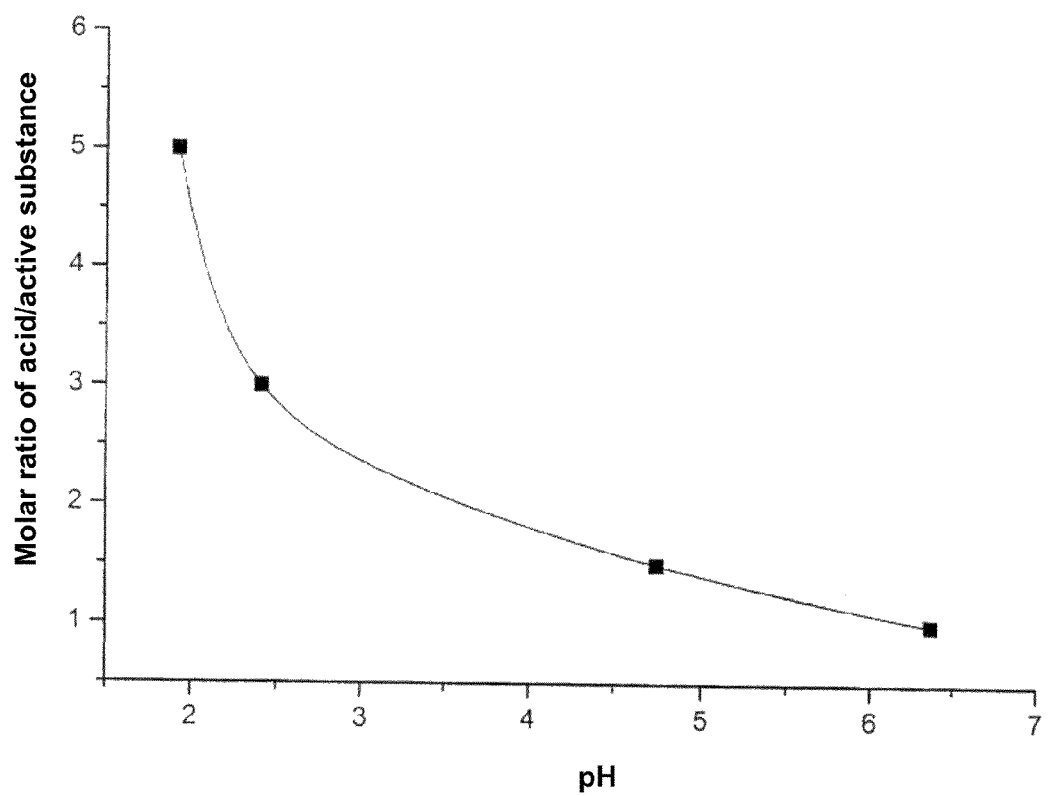

STORAGE STABLE PERFUSION SOLUTION FOR DIHYDROPTERIDINONES

APPLICATION DATA

This application is a continuation of U.S. application Ser. No. 11/197,927 filed Aug. 5, 2005, which also claims benefit to European Patent Application no. EP 04 019 363.3 filed Aug. 14, 2004.

FIELD OF INVENTION

The present invention relates to storage stable aqueous infusible or injectable solutions containing an active substance of formula (I)

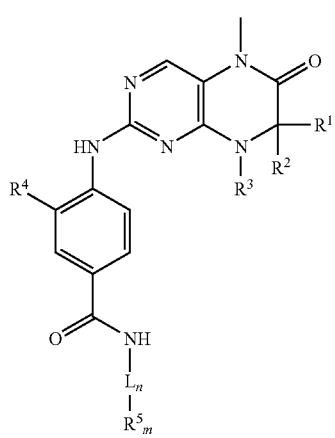

(I)

wherein the groups L, $R^1$, $R^2$, $R^3$, $R^4$ and $R^5$ have the meanings given in the claims and in the specification, and an amount of a physiologically acceptable acid or mixture of acids sufficient to dissolve the active substance and act as a stabiliser, optionally together with other formulating excipients suitable for parenteral administration, and a process for preparing the infusible or injectable solutions according to the invention.

BACKGROUND TO THE INVENTION

The dihydropteridinones of formula (I) according to the invention are an innovative new cytostatic active substance in the oncological treatment of fast-growing types of cancer. Usually, cytostatic medications are administered as parenteral preparations, even though their oral bioavailability may be perfectly adequate. The reason for this is that treatment with cytostatics is generally accompanied by a range of gastrointestinal side-effects which is frequently characterised by nausea, vomiting and/or diarrhoea, and consequently effective treatment by oral route would be jeopardised thereby.

These circumstances also apply to the dihydropteridinones of formula (I) and make it essential to prepare a solution for parenteral infusion or injection.

In the prior art EP 0219784 and WO 01/78732 describe methods of preparing and stabilising solutions for infusion containing ciprofloxacin by using one or more physiologically acceptable acid(s) of organic or inorganic origin. EP A 0287926 relates that the risk of particle formation can be greatly reduced by the use of highly pure grades of ciprofloxacin. EP 0143478 A1 describes the preparation of a stable hydrochloric acid solution of cisplatin, suitable for injection, which is particularly free from other additives. DE 197 03023 discloses that the stability of infusible solutions with regard to the formation of particulate impurities can be vastly improved by the use of glass containers with siliconised surfaces.

The aim of the present invention is to provide a stable infusible or injectable solution of dihydropteridinones of formula (I) for the desired dosage range tailored to treatment. As a further objective of the invention the stable infusible or injectable solution should be suitable both as a ready-to-use solution and as a concentrate for further dilution with solutions commonly used for parenteral administration such as for example isotonic NaCl solution, isotonic dextrose solution or Ringer lactate solution, to allow flexible adaptation of the dosage.

DESCRIPTION OF THE INVENTION

It has been found that, surprisingly, storage stable aqueous infusible or injectable solutions containing an active substance of general formula (I), which contain an amount of a physiologically acceptable acid or mixture of acids sufficient to dissolve the active substance and act as a stabiliser, optionally together with other formulating excipients suitable for parenteral administration, can be produced free from particles and with long-term stability, irrespective of the quality of the active substance in each case, and in particular irrespective of the contamination profile.

The present invention therefore relates to storage stable aqueous infusible or injectable solutions containing the active substance of general formula (I)

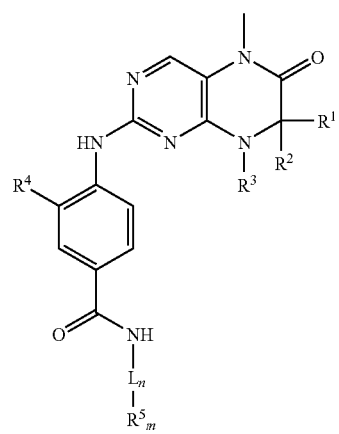

(I)

wherein
$R^1$, $R^2$ which may be identical or different, denote hydrogen or optionally substituted $C_1$-$C_6$-alkyl, or
$R^1$ and $R^2$ together denote a 2- to 5-membered alkyl bridge which may contain 1 to 2 heteroatoms,
$R^3$ denotes hydrogen or a group selected from among optionally substituted $C_1$-$C_{12}$-alkyl, $C_2$-$C_{12}$-alkenyl, $C_2$-$C_{12}$-alkynyl and $C_6$-$C_{14}$-aryl, or
a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl, $C_3$-$C_{12}$-heterocycloalkyl which contains 1 to 2 heteroatoms, and $C_3$-$C_{12}$-heterocycloalkenyl which contains 1 to 2 heteroatoms, or R$^1$ and R$^3$ or R$^2$ and R$^3$ together denote a saturated or unsaturated C$_3$-C$_4$-alkyl bridge which may contain 1 heteroatom, R$^4$ denotes a group selected from among hydrogen, —CN, hydroxy, —NR$_6$R$_7$ and halogen, or a group selected from among optionally substituted C$_1$-C$_6$-alkyl, C$_2$-C$_6$-alkenyl, C$_2$-C$_6$-alkynyl, C$_1$-C$_5$-alkyloxy, C$_2$-C$_5$-alkenyloxy, C$_2$-C$_5$-alkynyloxy, C$_1$-C$_6$-alkylthio, C$_1$-C$_6$-alkylsulphoxo and C$_1$-C$_6$-alkylsulphonyl, L denotes a linker selected from among optionally substituted C$_2$-C$_{10}$-alkyl, C$_2$-C$_{10}$-alkenyl, C$_6$-C$_{14}$-aryl, —C$_2$-C$_4$-alkyl-C$_6$-C$_{14}$-aryl, —C$_6$-C$_{14}$-aryl-C$_1$-C$_4$-alkyl, optionally bridged C$_3$-C$_{12}$-cycloalkyl and heteroaryl which contains 1 or 2 nitrogen atoms, n denotes 0 or 1, m denotes 1 or 2, R$^5$ denotes a group selected from among optionally substituted morpholinyl, piperidinyl, piperazinyl, piperazinylcarbonyl, pyrrolidinyl, tropenyl, R$^8$-diketomethylpiperazinyl, sulphoxomorpholinyl, sulphonylmorpholinyl, thiomorpholinyl, —NR$^8$R$^9$ and azacycloheptyl, R$^6$, R$^7$ which may be identical or different, denote hydrogen or C$_1$-C$_4$-alkyl, R$^8$, R$^9$ denote unsubstituted nitrogen substituents at R$^5$, which may be identical or different, either hydrogen or a group selected from among C$_1$-C$_6$-alkyl, —C$_1$-C$_4$-alkyl-C$_3$-C$_{10}$-cycloalkyl, C$_3$-C$_{10}$-cycloalkyl, C$_6$-C$_{14}$-aryl, —C$_1$-C$_4$-alkyl-C$_6$-C$_{14}$-aryl, pyranyl, pyridinyl, pyrimidinyl, C$_1$-C$_4$-alkyloxycarbonyl, C$_6$-C$_{14}$-arylcarbonyl, C$_1$-C$_4$-alkylcarbonyl, C$_6$-C$_{14}$-arylmethyloxycarbonyl, C$_6$-C$_{14}$-arylsulphonyl, C$_1$-C$_4$-alkylsulphonyl- and C$_6$-C$_{14}$-aryl-C$_1$-C$_4$-alkylsulphonyl, or the tautomers, racemates, enantiomers, diastereomers or optionally the physiologically effective derivatives or metabolites thereof and an amount of a physiologically acceptable acid or mixture of acids sufficient to dissolve the active substance and act as a stabiliser, optionally together with other formulating excipients suitable for parenteral administration.

Preferred storage stable solutions are those containing compounds of formula (I), wherein R$^1$ to R$^4$, R$^6$ and R$^7$ are as hereinbefore defined, and L denotes a linker selected from among optionally substituted C$_2$-C$_{10}$-alkyl, C$_2$-C$_{10}$-alkenyl, C$_6$-C$_{14}$-aryl, —C$_2$-C$_4$-alkyl-C$_6$-C$_{14}$-aryl, —C$_6$-C$_{14}$-aryl-C$_1$-C$_4$-alkyl, optionally bridged C$_3$-C$_{12}$-cycloalkyl and heteroaryl which contains 1 or 2 nitrogen atoms, n denotes 1, m denotes 1 or 2, R$^5$ denotes a group bound to L via a nitrogen atom, selected from among optionally substituted morpholinyl, piperidinyl, R$^8$-piperazinyl, pyrrolidinyl, tropenyl, R$^8$-diketomethylpiperazinyl, sulphoxomorpholinyl, sulphonylmorpholinyl, thiomorpholinyl, —NR$^8$R$^9$ and azacycloheptyl, and R$^8$, R$^9$ denote unsubstituted nitrogen substituents at R$^5$, which may be identical or different, which denote hydrogen or a group selected from among C$_1$-C$_6$-alkyl, —C$_1$-C$_4$-alkyl-C$_3$-C$_{10}$-cycloalkyl, C$_3$-C$_{10}$-cycloalkyl, C$_6$-C$_{14}$-aryl, —C$_1$-C$_4$-alkyl-C$_6$-C$_{14}$-aryl, pyranyl, pyridinyl, pyrimidinyl, C$_1$-C$_4$-alkyloxycarbonyl, C$_6$-C$_{14}$-arylcarbonyl, C$_1$-C$_4$-alkylcarbonyl, C$_6$-C$_{14}$-arylmethyloxycarbonyl, C$_6$-C$_{14}$-arylsulphonyl, C$_1$-C$_4$-alkylsulphonyl- and C$_6$-C$_{14}$-aryl-C$_1$-C$_4$-alkylsulphonyl, optionally in the form of the tautomers, racemates, enantiomers, diastereomers and mixtures thereof, and optionally the pharmacologically acceptable acid addition salts thereof.

Also preferred are storage stable solutions containing compounds of formula (I), wherein R$^1$ to R$^4$, R$^6$ and R$^7$ are as hereinbefore defined, and L denotes a linker selected from among optionally substituted C$_2$-C$_{10}$-alkyl, C$_2$-C$_{10}$-alkenyl, C$_6$-C$_{14}$-aryl, —C$_2$-C$_4$-alkyl-C$_6$-C$_{14}$-aryl, —C$_6$-C$_{14}$-aryl-C$_1$-C$_4$-alkyl, optionally bridged C$_3$-C$_{12}$-cycloalkyl and heteroaryl which contains 1 or 2 nitrogen atoms, n denotes 0 or 1, m denotes 1 or 2, R$^5$ denotes a group which is bound to L via a carbon atom, selected from among R$^8$-piperidinyl, R$^8$R$^9$-piperazinyl, R$^8$-pyrrolidinyl, R$^8$-piperazinylcarbonyl, R$^8$-tropenyl, R$^8$-morpholinyl and R$^8$-azacycloheptyl, and R$^8$, R$^9$ denote unsubstituted nitrogen substituents at R$^5$, which may be identical or different, which denote hydrogen or a group selected from among C$_1$-C$_6$-alkyl, —C$_1$-C$_4$-alkyl-C$_3$-C$_{10}$-cycloalkyl, C$_3$-C$_{10}$-cycloalkyl, C$_6$-C$_{14}$-aryl, —C$_1$-C$_4$-alkyl-C$_6$-C$_{14}$-aryl, pyranyl, pyridinyl, pyrimidinyl, C$_1$-C$_4$-alkyloxycarbonyl, C$_6$-C$_{14}$-arylcarbonyl, C$_1$-C$_4$-alkylcarbonyl, C$_6$-C$_{14}$-arylmethyloxycarbonyl, C$_6$-C$_{14}$-arylsulphonyl, C$_1$-C$_4$-alkylsulphonyl- and C$_6$-C$_{14}$-aryl-C$_1$-C$_4$-alkylsulphonyl, optionally in the form of the tautomers, racemates, enantiomers, diastereomers and mixtures thereof, and optionally the pharmacologically acceptable acid addition salts thereof.

Particularly preferred are storage stable solutions containing compounds of formula (I), wherein L, m, n and R$^3$ to R$^9$ are as hereinbefore defined, and R$^1$, R$^2$ which may be identical or different denote a group selected from among hydrogen, Me, Et and Pr, or R$^1$ and R$^2$ together form a C$_2$-C$_4$-alkyl bridge, optionally in the form of the tautomers, racemates, enantiomers, diastereomers and mixtures thereof, and optionally the pharmacologically acceptable acid addition salts thereof.

Particularly preferred are storage stable solutions containing compounds of formula (I), wherein R$^1$, R$^2$, m, n and R$^5$ to R$^8$ are as hereinbefore defined, and R$^3$ denotes a group selected from among optionally substituted C$_1$-C$_{10}$-alkyl, C$_3$-C$_7$-cycloalkyl, C$_3$-C$_6$-heterocycloalkyl and C$_6$-C$_{14}$-aryl, or R$^1$ and R$^3$ or R$^2$ and R$^3$ together denote a saturated or unsaturated C$_3$-C$_4$-alkyl bridge which may contain 1 to 2 heteroatoms, and R$^4$ denotes a group selected from among hydrogen, OMe, OH, Me, Et, Pr, OEt, NHMe, NH$_2$, F, CL, Br, O-propargyl, O-butynyl, CN, SMe, NMe$_2$, CONH$_2$, ethynyl, propynyl, butynyl and allyl, and L denotes a linker selected from among optionally substituted phenyl, phenylmethyl, cyclohexyl and branched C$_1$-C$_6$-alkyl, optionally in the form of the tautomers, racemates, enantiomers, diastereomers and mixtures thereof, and optionally the pharmacologically acceptable acid addition salts thereof.

The invention also relates to a storage stable solution containing a dihydropteridinone of general formula (I) as hereinbefore described, the dihydropteridinone being selected from among the following dihydropteridinones of general formula (I)

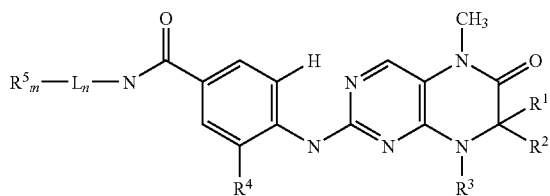
| Ex. | R¹ | R² | Config. R¹ or R² | R³ | R⁴ | Lₙ—R⁵ₘ |
|---|---|---|---|---|---|---|
| 27 | H | X₂⟍CH₃ | R | X₃ H₃C–CH–CH₃ | X₄ O–CH₃ | X₅-cyclohexyl-N-morpholine |
| 44 | H | X₂⟍CH₃ | R | X₃-cyclopentyl | H | X₅-(1-methylpiperidin-4-yl) |
| 55 | H | X₂⟍CH₃ | R | X₃-cyclopentyl | CH₃–O–X₄ | X₅ H₃C–C(CH₃)–CH₂–N(pyrrolidinyl) |
| 58 | H | X₂⟍CH₃ | R | X₃-cyclopentyl | CH₃–O–X₄ | X₅ CH₂CH₃, H₃C, CH₃ quaternary C–CH₂–N(CH₃)₂ |
| 102 | H | X₂⟍CH₃ | R | X₃ H₃C–CH–CH₃ | CH₃–O–X₄ | X₅-(1-benzylpiperidin-4-yl) |

-continued
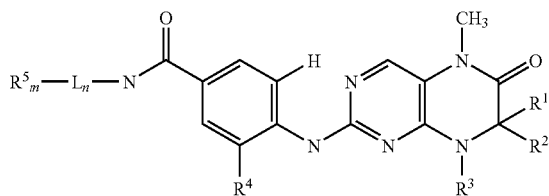
| Ex. | R¹ | R² | Config. R¹ or R² | R³ | R⁴ | Lₙ—R⁵ₘ |
|---|---|---|---|---|---|---|
| 103 | H | X₂◂CH₃ | R | X₃-cyclopentyl | CH₃-O-X₄ | X₅-(1-benzylpiperidin-4-yl) |
| 105 | H | X₂◂CH₃ | R | X₃-cyclopentyl | X₄-O-CH₃ | X₅-[4-(4-(cyclopropylmethyl)piperazin-1-yl)cyclohexyl] |
| 110 | H | X₂–CH₂CH₃ | R | X₃-CH(CH₃)₂ (isopropyl) | X₄-O-CH₃ | X₅-[4-(4-(cyclopropylmethyl)piperazin-1-yl)cyclohexyl] |
| 115 | H | X₂◂CH₃ | R | X₃-cyclohexyl | CH₃-O-X₄ | X₅-(1-benzylpiperidin-4-yl) |

-continued

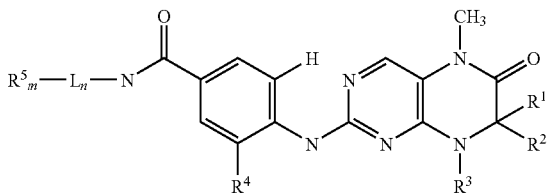

| Ex. | R¹ | R² | Config. R¹ or R² | R³ | R⁴ | $L_n$—$R^5_m$ |
|---|---|---|---|---|---|---|
| 133 | H | $X_2$—CH₃ | R | $X_3$-cyclopentyl | $X_4$-O-CH₃ | $X_5$-cyclohexyl-N-morpholine |
| 134 | H | $X_2$—CH₃ | R | $X_3$-cyclopentyl | $X_4$-O-CH₃ | $X_5$-cyclohexyl-N-piperazine-N-phenyl |
| 234 | H | $X_1$—CH₃ | R | $X_3$-CH(CH₃)₂ | $X_4$-O-CH₃ | $X_5$-cyclohexyl-N-(2,6-dimethylmorpholine) |
| 240 | H | $X_1$—CH₃ | R | $X_3$-cyclohexyl | CH₃-O-$X_4$ | $X_5$-C(CH₃)₂-CH₂-N(CH₃)₂ | while the abbreviations $X_1$, $X_2$, $X_3$, $X_4$ and $X_5$ used in the Table in each case denote a link to a position in the general formula listed in the Table instead of the corresponding groups R¹, R², R³, R⁴ and L-R⁵.

Long-term stability is defined as a shelf-life of at least 12 months at 25° C./60% r.h. and 30° C./70% r.h., preferably at least 36 months at 25°/60% r.h. and 30° C./70% r.h.

The infusible or injectable solutions according to the invention, apart from the addition of a physiologically acceptable acid or mixture of acids, may be free from solubilising additives or organic cosolvents, particularly organic cosolvents.

Preferred aqueous infusible or injectable solutions are those wherein the content of dissolved active substance of formula (I) is 0.1 mg to 10.0 mg, particularly preferably 0.5 to 5 mg, in 1 ml of infusible or injectable solution.

Also preferred are aqueous infusible or injectable solutions, wherein one or more acids used as storage and dilution stabilisers are selected from among hydrochloric acid, acetic acid, hydroxyacetic acid, methanesulphonic acid, ethanesulphonic acid, phosphoric acid, nitric acid, sulphuric acid, citric acid, tartaric acid, fumaric acid, succinic acid, glutaric acid, adipic acid, propionic acid, ascorbic acid, maleic acid, malic acid, glutamic acid, gluconic acid, glucuronic acid, galacturonic acid and lactic acid, preferably acetic acid, hydrochloric acid, phosphoric acid, tartaric acid, citric acid and fumaric acid, particularly preferably hydrochloric acid, citric acid and acetic acid.

For reasons of pH compatibility, as is evident from FIG. 1, aqueous infusible or injectable solutions are preferred wherein the molar ratio of the physiologically acceptable acid or mixture of acids to the active substance is at most 3:1, preferably 1.25:1 to 3:1, particularly preferably 1.5:1 to 3:1, in order to ensure that the pH is above 2.4.

Preferably the invention also relates to infusible or injectable solutions which contain 0.1 mg to 10.0 mg active substance per milliliter of aqueous solution and up to 3.0 mol of hydrochloric acid, based on one mol of active substance. The amounts of hydrochloric acid are preferably 1.25 mol to 3.0 mol, particularly 1.5 to 2.4 mol.

The invention also relates to infusible or injectable solutions of 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide which contain 1.6 to 2.0 mol hydrochloric acid per mol of active substance.

The infusible or injectable solutions according to the invention may also be modified so as to contain up to 10 mg/ml of the active substance, and up to 1 mol hydrochloric acid per mol of active substance, as well as one or more other physiologically acceptable acid(s), with the proviso that the total amount of acid is at least 1.25 mol per mol of active substance, but does not exceed 3.0 mol per mol active substance.

The minimum amount of acid needed per mol of active substance depends on the active substance concentration, and the acid(s) used, and is thus not constant. However, it may be determined within the limits according to the invention by simple tests as described for example in EP 0219784 and WO 01/78732.

Particularly preferred are aqueous infusible or injectable solutions which contain one or more other formulation aids selected from among complexing agents, crystallisation inhibitors, thickeners, isotonic agents, preservatives, light protecting agents and antioxidants.

Suitable complexing agents are e.g. genuine and substituted cyclodextrins, EDTA, albumins, as well as citric acid and the salts and derivatives thereof.

Suitable crystallisation inhibitors are e.g. PVP, cellulose derivatives, alginates, poloxamers and polysorbates.

Suitable thickeners are for example dextrans, glycerol and soluble cellulose derivatives, particularly carboxymethylcellulose and the salts thereof, as well as hydroxyalkyl celluloses.

Suitable isotonic agents are for example NaCl, mannitol, sorbitol, xylitol, saccharose, lactose, glucose and glycerol, preferably NaCl, mannitol, glucose, saccharose and glycerol, particularly preferably NaCl, mannitol and glucose.

Suitable preservatives are for example the esters of p-hydroxybenzoic acid, benzylalcohol, sorbic acid and benzoic acid.

Suitable light protecting agents are for example derivatives of p-hydroxybenzoic acid as well as cinnamic acid and the derivatives thereof.

A suitable antioxidant is for example ascorbic acid and the salts thereof.

Also particularly preferred are aqueous infusible or injectable solutions wherein the osmolality of the infusible or injectable solutions is 200-600 mOsmol/kg, preferably 260-350 mOsmol/kg. They may be prepared using isotonic agents such as NaCl, mannitol, sorbitol, glucose, saccharose, xylitol, fructose and glycerol or mixtures of the above-mentioned substances. Preferred are infusible or injectable solutions which contain, in addition to the active substance, water, acid(s) and other formulation aids, an amount of NaCl or other isotonic agent such that a solution is obtained which is isotonic with the tissue fluid of the human or animal body or slightly hypotonic or hypertonic solution.

Most preferred are aqueous infusible or injectable solutions which have a pH in the range from 2.4 to 5.3, preferably from 3.5 to 5.0, particularly preferably from 3.9 to 4.5.

The infusible or injectable solutions according to the invention are also suitable for dilution with standard commercial infusion or injection carrier solutions for supplying electrolyte without carbohydrates, such as isotonic NaCl solution, isotonic glucose solution, Ringer lactate solution and the like (Red List 2004, Verzeichnis des Bundesverbandes der Pharmazeutischen Industrie e.V., [Directory of Drug Products of the Members of the Federal Association of the Pharmaceutical Industry], Editio Cantor, Aulendorf/Württ., main groups 52.1 and 52.2.1) to give the desired concentration or dose without having any physical or chemical incompatibilities.

Also most preferred are aqueous infusible or injectable solutions which contain 1.25 to 3.0 mol, preferably 1.5 to 2.4 mol, of hydrochloric acid per mol of active substance, based on 100 ml of infusible or injectable solution, 0.75 to 1.2 g NaCl, preferably 0.85 to 0.95 g NaCl, and have an osmolality of 260 to 350 mOsmol/kg and a pH of 3.5 to 5.0.

The invention further relates to lyophilisates, concentrates and suspensions which by the addition of water yield one of the aqueous infusible or injectable solutions according to the invention.

The invention also relates to the infusible or injectable solutions according to the invention for use as pharmaceutical compositions with an antiproliferative activity.

The invention further relates to the use of the infusible or injectable solutions according to the invention for preparing a pharmaceutical composition for the treatment of tumoral diseases, infections, inflammatory and autoimmune diseases.

The invention further relates to a method for the treatment and/or prevention of tumoral diseases, infections, inflammatory and autoimmune diseases, preferably tumoral diseases, in which an effective amount of an infusible or injectable solution according to the invention is administered to a patient.

The invention further relates to the use of the infusible or injectable solutions according to the invention, which corresponds to a dosage range of from 0.1 to 50 mg active substance/kg body weight, preferably 0.5 to 25 mg active substance/kg body weight.

The infusible or injectable solutions according to the invention may be stored in suitable glass containers for parenteral preparations or in flexible plastic containers, preferably non-PVC materials based e.g. on polyolefin, with removable volumes of 20 to 1000 ml, preferably 50 to 500 ml. The containers may be designed so as to provide particular protection for the infusible or injectable solutions according to the invention, e.g. to protect them from light or oxygen.

Special surface treatment of the primary packaging (e.g. (stoved) siliconisation of the surfaces of glass containers) to improve the stability of the infusible or injectable solutions according to the invention is neither necessary nor harmful. Flexible plastic containers may contain additional protection, e.g. in the form of aluminium packaging.

The infusible or injectable solutions according to the invention are suitable for terminal sterilisation, e.g. with pressurised steam, and can thus be made sterile and free from pyrogens in a particularly economical manner and with high product safety (low risk of contamination).

The infusible or injectable solution according to the invention may be prepared by methods of producing aqueous liquid formulations known from the literature.

Thus, the present invention relates to a process for preparing the infusible or injectable solutions according to the invention, containing 0.1 to 10 mg per milliliter of the active substance of formula (I). The process is characterised in that a suitable amount of active substance, optionally in the form of a salt, is combined with an anionic counter-ion, a hydrate or hydrates of a salt, or mixtures of these salts/hydrates with the quantity of a physiologically acceptable acid or mixture of acids which constitutes an excess in relation to the precise [amount needed] to dissolve the active substance or the salts or hydrates thereof and to prevent physical instabilities, other formulating excipients are optionally added, and the preparation is made up with water (for injections) such that a range of concentrations of from 0.1 to 10 mg of active substance per milliliter of infusible or injectable solution is obtained.

When preparing the infusible or injectable solutions care should also be taken to ensure that the solution has the properties mentioned above regarding pH, amounts of acid, and osmolality. If a salt is used it is advantageous to use an acid the anion of which corresponds to the anion of the salt or salt hydrate of the active substance.

The active substance or the salt or hydrate thereof is optionally suspended in water, and up to 3.0 mol of physiologically acceptable acid or mixture of acids, preferably hydrochloric acid, are added per mol of active substance.

Finally, the other formulating excipients are added, particularly isotonic agents, preferably NaCl, which may optionally also be produced by a neutralising reaction in the formulation mixture, before it is adjusted to the desired active substance concentration with water.

The pH of the infusible or injectable solutions according to the invention can be adjusted to the pH values specified above with (physiologically) acceptable acids and/or bases, particularly NaOH.

To speed up the production process, particularly to dissolve the solid ingredients, the solutions may be heated slightly as a whole or in parts, preferably to temperatures between 20° C. and 80° C.

The solutions according to the invention may be prepared particularly economically using concentrated solutions. The amount of active substance required for a preparation is combined with the majority (>90%) of the physiologically acceptable acid or mixture of acids and dissolved, optionally with gentle heating and/or the addition of a small amount of water. This concentrate is then diluted with water before the other formulating excipients are added, and lastly made up to the nominal weight with the remainder of the acid(s) or water.

After the preparation of the solution it is generally filtered through a 0.2 μm membrane or deep filter, although finally it is terminally sterilised with pressurised steam in order to remove any particles and/or pyrogens which may be present.

Details of suitable filtration methods are known from the prior art (M. J. Groves, Parenteral Technology Manual, Interpharm Press Inc., 2. ed. 1988). The number of particles is limited to what the regulations specify and is economically viable, for example 6000 particles≧10 μm and 600 particles≧25 μm per package (package≦100 mL) or 25 particles≧10 μm and 3 particles≧25 μm per milliliter (package>100 mL), USP 27 <788>.

The solutions according to the invention have good stability on storage which is not limited either by the number of particles in the visible and subvisual range, or by significant active substance breakdown reactions.

The solutions according to the invention have sufficient local compatibility with respect to the pharmacodynamic properties of the active substance, and are not haemolytic.

The infusible or injectable solutions according to the invention are intended to be illustrated by the Examples that follow. The Examples serve purely as an illustration and are not to be construed in a limiting capacity.

FIG. 1 shows the dependency of the pH of the ready-to-use solution on the molar ratio of acid/mixture of acids to active substance. The active substance here is 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide (Example 46 from Table 1).

For reasons of improved local compatibility for an iv infusion/injection the maximum molar ratio of acid(s) to active substance in the infusible or injectable solution according to the invention is restricted to a maximum of 3:1, in order to ensure a pH above 2.4.

EXAMPLES OF PARENTERAL SOLUTIONS FOR INFUSION OR INJECTION

The abbreviation WFI denotes Water For Injections.

In the following general Example 1 the active substance is one of the dihydropteridinones of general formula (I) as hereinbefore described.

General Example 1

| | |
|---|---|
| active substance | 1-10 mg/ml |
| organic or inorganic acid, or acid mixture | 1.0-3.0 mol (calculated on the basis of the active substance) |
| isotonic agent (e.g. NaCl/mannitol) | e.g. 9 mg/ml or 50 mg/ml |
| WFI ad | final volume, e.g. 1.0 ml |
| pH | 3.0-4.5 |

In the following Examples the active substance is 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide (Example 46 from Table 1).

Example 2

| | |
|---|---|
| active substance | 2 mg/ml |
| hydrochloric acid 1N | 6.8 μl |
| NaCl | 0.009 g/ml |
| WFI ad | 1 ml |
| pH | 4.5 |
| mOsmol/kg | 295 |

Example 3

| | |
|---|---|
| active substance | 10.0000 g |
| hydrochloric acid 1N | 36.6735 g |
| NaCl | 45.0000 g |
| WFI | 4934.8265 g |
| pH | 4.3 |
| mOsmol/kg | 300 |

Example 4

| | |
|---|---|
| active substance | 500 mg |
| hydrochloric acid 1N | 1.6 ml |
| NaCl | 450.0 mg |
| WFI ad | 50 ml |
| pH | 4.0 |
| mOsmol/kg | 290 |

Example 5

| | |
|---|---|
| active substance | 0.5 mg |
| hydrochloric acid 1N | 1.705 μl |
| NaCl | 9 mg |
| WFI ad | 1 ml |
| pH | 4.8 |
| mOsmol/kg | 285 |

Example 6

| | |
|---|---|
| active substance | 1 mg |
| hydrochloric acid 1N | 3.6125 μl |
| NaCl | 0.009 g |
| WFI ad | 1 ml |
| pH | 4.8 |
| mOsmol/kg | 295 |

Example 7

| | |
|---|---|
| active substance | 2 mg |
| phosphoric acid (85%) | 0.440 μl |
| NaCl | 9 mg |
| WFI ad | 1 ml |
| pH | 4.0 |
| mOsmol/kg | 298 |

Example 8

| | |
|---|---|
| active substance | 100 mg |
| acetic acid | 16.4 μl |
| dextrose | 2.5 g |
| WFI ad | 50 ml |
| pH | 4.4 |
| mOsmol/kg | 305 |

Example 9

| | |
|---|---|
| active substance | 10 mg |
| tartaric acid | 4.32 mg |
| mannitol | 0.25 g |
| WFI ad | 5 ml |
| pH | 4.0 |
| mOsmol/kg | 298 |

Example 10

| | |
|---|---|
| active substance | 2 mg |
| citric acid | 1.104 mg |
| NaCl | 9 mg |
| WFI ad | 1 ml |
| pH | 4.5 |
| mOsmol/kg | 295 |

Example 11

| | |
|---|---|
| active substance | 2 mg |
| hydrochloric acid 1N | 6.8 μl |
| acetic acid | 0.501 mg |
| Na-acetate | 0.2260 mg |
| NaCl | 9 mg |
| WFI ad | 1 ml |
| pH | 4.0 |
| mOsmol/kg | 305 |

In the following Examples the active substance is N-[trans-4-[4-(cyclopropylmethyl)-1-piperazinyl]cyclohexyl]-4-[[(7R)-7-ethyl-5,6,7,8-tetrahydro-5-methyl-8-(1-methyl-ethyl)-6-oxo-2-pteridinyl]amino]-3-methoxy-benzamide (Example 110 from Table 1).

Example 12

| | |
|---|---|
| active substance* 3 HBr | 2 mg/ml* (calculated as base) |
| NaCl | 9 mg/ml |
| WFI ad | 1.0 ml |
| pH | 3.5 |

Example 13

| active substance*<br>3 HCl | 2 mg/ml*<br>(calculated as base) |
|---|---|
| NaCl | 9 mg/ml |
| WFI ad | 1.0 ml |
| pH | 3.4 |

Example 14

| active substance | 500 mg |
|---|---|
| phosphoric acid 85% | 157.5 mg |
| NaCl | 2.250 g |
| WFI ad | 250.0 ml |
| pH | 3.2 |

Example 15

| active substance | 10 mg |
|---|---|
| tartaric acid | 4.85 mg |
| NaCl | 45 mg |
| WFI ad | 5 ml |
| pH | 3.5 |

Example 16

| active substance | 2 mg/ml |
|---|---|
| acetic acid | 0.39 mg |
| NaCl | 0.009 g |
| WFI ad | 1 ml |
| pH | 3.4 |

Example 17

| active substance | 2 mg |
|---|---|
| citric acid | 1.24 mg |
| mannitol | 50 mg |
| WFI ad | 1 ml |
| pH | 3.5 |

The compounds according to the invention may be prepared by the methods of synthesis A described hereinafter, whereby the substituents of general formulae (A1) to (A9) have the above meanings. This method is to be understood as an illustration of the invention without limiting it to the content thereof.

Process A

Step 1A

A compound of formula (A1) is reacted with a compound of formula (A2) to yield a compound of formula (A3) (Diagram 1A). This reaction may be carried out according to WO 00/43369 or WO 00/43372. Compound (A1) is commercially available, for example from City Chemical LLC, 139 Allings Crossing Road, West Haven, Conn., 06516, USA. Compound (A2) may be prepared by methods known from the literature, e.g. from (a) F. Effenberger, U. Burkhart, J. Willfahrt *Liebigs Ann. Chem.* 1986, 314-333, (b) T. Fukuyama, C.-K. Jow, M. Cheung, *Tetrahedron Lett.* 1995, 36, 6373-6374, (c) R. K. Olsen, *J. Org. Chem.* 1970, 35, 1912-1915, (d) F. E. Dutton, B. H. Byung *Tetrahedron Lett.* 1998, 30, 5313-5316 or (e) J. M. Ranajuhi, M. M. Joullie *Synth. Commun.* 1996, 26, 1379-1384.

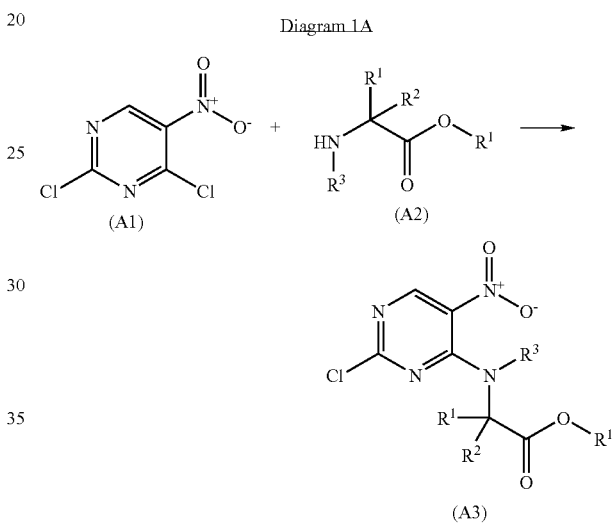

Diagram 1A

In Step 1A, 1 equivalent of the compound (A1) and 1 to 1.5 equivalents, preferably 1.1 equivalents of a base, preferably potassium carbonate, potassium hydrogen carbonate, sodium carbonate, sodium hydrogen carbonate or calcium carbonate, particularly preferably potassium carbonate, are stirred in a diluent, optionally mixed with water, for example acetone, tetrahydrofuran, diethyl ether, cyclohexane, petroleum ether or dioxane, preferably cyclohexane or diethyl ether.

At a temperature of 0 to 15° C., preferably 5 to 10° C., 1 equivalent of an amino acid of formula (A2) dissolved in an organic solvent, for example acetone, tetrahydrofuran, diethyl ether, cyclohexane or dioxane, is added dropwise. The reaction mixture is heated to a temperature of 18° C. to 30° C., preferably about 22° C., with stirring and then stirred for a further 10 to 24 hours, preferably about 12 hours. Then the diluent is distilled off, the residue is combined with water and the mixture is extracted two to three times with an organic solvent, for example, diethyl ether or ethyl acetate, preferably ethyl acetate. The combined organic extracts are dried and the solvent is distilled off. The residue (compound A3) may be used in Step 2 without any prior purification.

Step 2A

The compound (A3) obtained in Step 1A is reduced at the nitro group and cyclised to form the compound of formula (A4) (Diagram 2A).

Diagram 2A

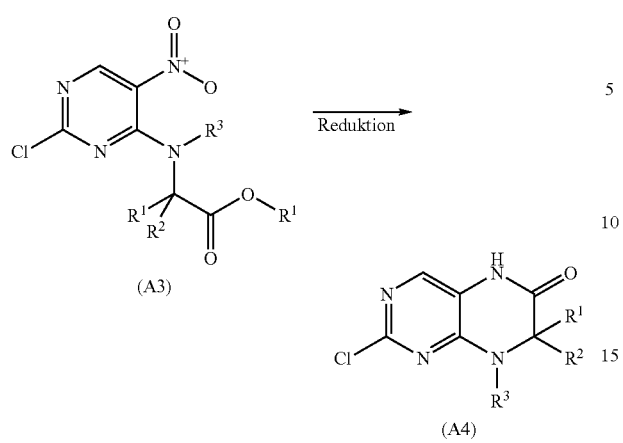

Diagram 3A

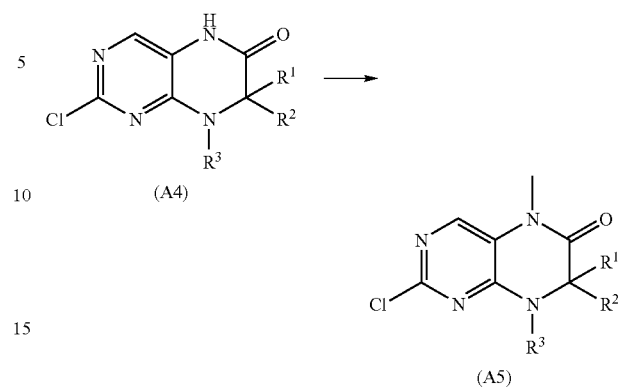

In Step 2A 1 equivalent of the nitro compound (A3) is dissolved in an acid, preferably glacial acetic acid, formic acid or aqueous hydrochloric acid, preferably glacial acetic acid, and heated to 50 to 70° C., preferably about 60° C. Then a reducing agent, for example zinc, tin or iron, preferably iron powder, is added until the exothermic reaction has ended and the mixture is stirred for 0.2 to 2 hours, preferably 0.5 hours, at 100 to 125° C., preferably at about 117° C. After cooling to ambient temperature the iron salt is filtered off and the solvent is distilled off. The residue is taken up in a solvent or mixture of solvents, for example ethyl acetate or dichloromethane/methanol 9/1 and semisaturated NaCl solution and filtered through kieselguhr for example. The organic phase is dried and evaporated down. The residue (compound (A4)) may be purified by chromatography or by crystallisation or used as the crude product in Step 3A of the synthesis.

Step 3A

The compound (A4) obtained in Step 2A may be reacted by electrophilic substitution according to Diagram 3A to form the compound of formula (A5).

In Step 3A 1 equivalent of the amide of formula (A4) is dissolved in an organic solvent, for example dimethylformamide or dimethylacetamide, preferably dimethylacetamide, and cooled to about −5 to 5° C., preferably 0° C.

Then 0.9 to 1.3 equivalents of sodium hydride and 0.9 to 1.3 equivalents of a methylating reagent, for example methyliodide, are added. The reaction mixture is stirred for 0.1-3 hours, preferably about 1 hour, at about 0 to 10° C., preferably at about 5° C., and may optionally be left to stand for a further 12 hours at this temperature range. The reaction mixture is poured onto ice water and the precipitate is isolated. The residue (compound (A5)) may be purified by chromatography, preferably on silica gel, or by crystallisation or used as the crude product in Step 4A of the synthesis.

Step 4A

The amination of the compound (A5) obtained in Step 3A to form the compound of formula (A9) (Diagram 4A) may be carried out according to the methods of variants 4.1 A known from the literature from e.g. (a) M. P. V. Boarland, J. F. W. McOmie *J. Chem. Soc.* 1951, 1218-1221 or (b) F. H. S. Curd, F. C. Rose *J. Chem. Soc.* 1946, 343-348, and 4.2 A from e.g. (a) Banks *J. Am. Chem. Soc.* 1944, 66, 1131, (b) Ghosh and Dolly *J. Indian Chem. Soc.* 1981, 58, 512-513 or (c) N. P. Reddy and M. Tanaka *Tetrahedron Lett.* 1997, 38, 4807-4810.

Diagram 4A

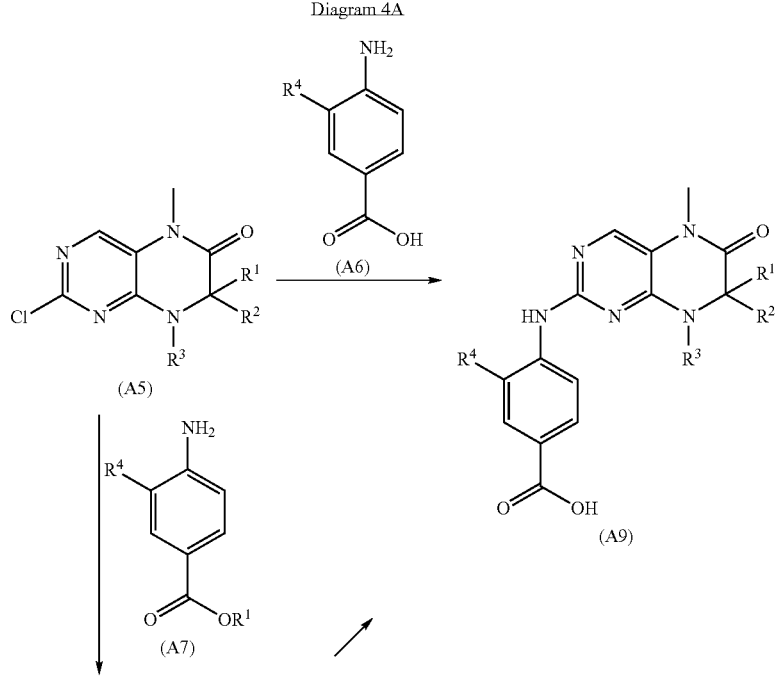

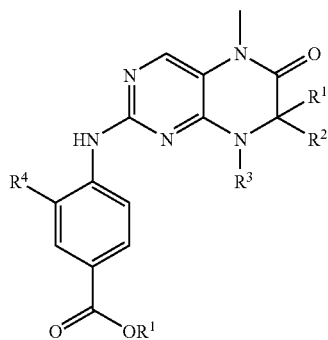

(A8)

For example in variant 4.1 A, 1 equivalent of the compound (A5) and 1 to 3 equivalents, preferably about 2 equivalents of the compound (A6) may be heated without a solvent or with an organic solvent such as for example sulpholane, dimethylformamide, dimethylacetamide, toluene, N-methylpyrrolidone, dimethylsulphoxide, or dioxane, preferably sulpholane over 0.1 to 4 hours, preferably 1 hour, at 100 to 220° C., preferably at about 160° C. After cooling the product (A9) is crystallised by the addition of org. solvents or mixtures of solvents, e.g. diethyl ether/methanol, ethyl acetate, methylene chloride, or diethyl ether, preferably diethyl ether/methanol 9/1, or purified by chromatography.

For example in variant 4.2 A, 1 equivalent of the compound (A5) and 1 to 3 equivalents of the compound (A6) are refluxed for 1 to 48 hours, preferably about 5 hours, with acid, for example 1-10 equivalents of 10-38% hydrochloric acid and/or an alcohol such as ethanol, propanol or butanol, preferably ethanol, with stirring.

The precipitated product (A9) is filtered off and optionally washed with water, dried and crystallised from a suitable org. solvent.

For example in variant 4.3 A, 1 equivalent of the compound (A5) and 1 to 3 equivalents of the compound (A7) is dissolved in a solvent, for example toluene or dioxane and combined with a phosphine ligand, for example 2, 2'-bis-(diphenylphosphino)-1,1'-binaphthyl and a palladium catalyst, for example tris(dibenzylideneacetone)-dipalladium(0) and a base, for example caesium carbonate, and refluxed for 1-24 h, preferably 17 h. The reaction mixture is purified on silica gel for example and the product (A8) is isolated from the solution or obtained by suitable crystallisation.

The product (A8) is dissolved in a suitable solvent, for example dioxane, and mixed with acid, for example semiconcentrated hydrochloric acid, for example in a solvent to an acid ratio of 3:1. Then the mixture is refluxed for 1-48 h, for example 12 h, and the precipitate formed is isolated. If desired the product (A9) is purified by crystallisation.

Step 5A

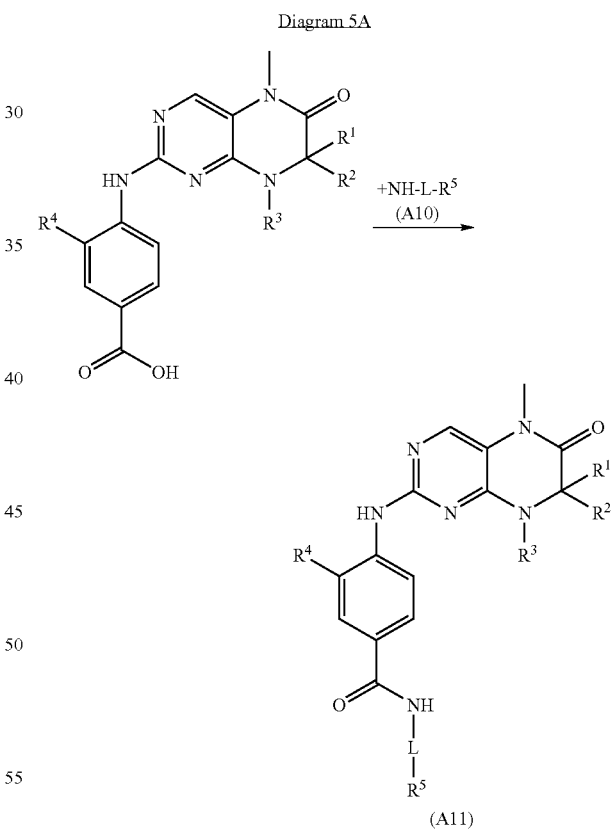

Diagram 5A

For example, 1 equivalent of the compound (A9) is dissolved with 1 equivalent of an activating reagent, for example O-benzotriazolyl-N,N,N',N'-tetramethyluronium tetrafluoroborate (TBTU) and a base, for example about 1.5 equivalents, diisopropylethylamine (DIPEA) in an organic diluent, for example dichloromethane, tetrahydrofuran, dimethylformamide, N-methylpyrrolidone, dimethylacetamide, preferably dichloromethane or dimethylformamide. After the addition of 1 equivalent of the amine (A10) the reaction mixture is stirred for 0.1 to 24 hours, preferably about 2 hours at 20° C. to 100° C. The product of formula (A11) is obtained for example by crystallisation or chromatographic purification.

The compounds of general formula (I) may be synthesised analogously to the following synthesis examples. These Examples should, however, only be regarded as an illustration of the procedures according to the invention without restricting the invention to their subject matter.

The preparation of some intermediate compounds used to synthesise the Examples will also be described hereinafter.

Preparation of the Acids

In order to synthesise the compounds Ex. 94 and Ex. 95 first of all an intermediate compound Z1

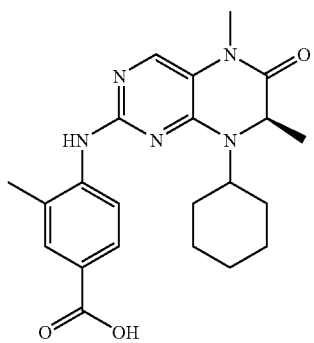

is prepared as described hereinafter.

50.0 g (0.48 mol) D-alanine methylester×HCl and 49.1 g (0.50 mol) cyclohexanone are placed in 300 mL dichloromethane and then combined with 41.0 g (0.50 mol) sodium acetate and 159.0 g (0.75 mol) sodium triacetoxyborohydride. The mixture is stirred overnight and then 300 mL of 10% sodium hydrogen carbonate solution are added. The aqueous phase is extracted with dichloromethane. The combined organic phases are washed with 10% sodium hydrogen carbonate solution, dried over $Na_2SO_4$ and evaporated down.

Yield: 72.5 g of a compound Z1a (clear liquid)

72.5 g of the compound Z1a are placed in 500 mL water and 76.6 g (0.39 mol) 2,4-dichloro-5-nitropyrimidine in 500 mL diethyl ether are added. At a temperature of −5° C. 100 mL 10% potassium hydrogen carbonate solution are added dropwise. The mixture is stirred for 3 h at −5° C. and for a further 12 h at ambient temperature. The organic phase is separated off and dried over $Na_2SO_4$. During evaporation the product crystallises out.

Yield: 48.0 g of a compound Z1b (yellow crystals)

48.0 g of the compound Z1b are dissolved in 350 mL glacial acetic acid and heated to 60° C. 47.5 g iron powder are added batchwise, while the temperature rises to 105° C. The reaction mixture is stirred for three hours at 80° C., then filtered hot through cellulose and evaporated down. The residue is stirred in water and ethyl acetate, suction filtered and the light grey precipitate is washed with ethyl acetate. The filtrate is washed with dilute ammonia and water, the organic phase is dried over $Na_2SO_4$, filtered through activated charcoal and evaporated down. More light grey solid is obtained.

Yield: 29.5 g of a compound Z1c (light grey crystals)

32.1 g of the compound Z1c are placed in 300 mL dimethylacetamide and combined with 13 mL (0.2 mol) methyliodide. At −5° C. 6.4 g (0.16 mol) sodium hydride are added batchwise as a 60% dispersion in mineral oil. After 2 h the reaction mixture is poured onto 800 mL ice water. The precipitate formed is suction filtered and washed with petroleum ether.

Yield: 33.0 g of a compound Z1d (beige crystals)

4.0 g of the compound Z1d and 2.3 g (15 mmol) of 4-amino-3-methylbenzoic acid are suspended in 50 mL ethanol and 120 mL water, combined with 2 mL conc. hydrochloric acid and refluxed for 48 h. The precipitate formed on cooling is suction filtered and washed with water, ethanol and diethyl ether.

Yield: 2.9 g of a compound Z1 (colourless crystals)

To synthesise the compounds Ex. 188 and Ex. 203 first of all an intermediate compound Z2

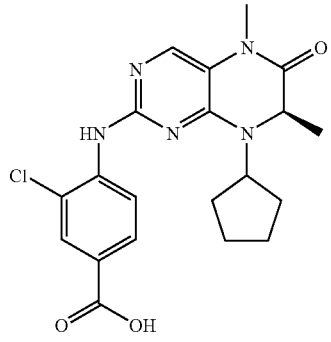

is prepared as described below.

A solution of 128.2 g (0.83 mol) D-alanine ethylester×HCl and 71.5 g (0.85 mol) cyclopentanone in 1500 mL dichloromethane is combined with 70.1 (0.85 mol) sodium acetate and 265.6 g (1.25 mol) sodium triacetoxyborohydride. The reaction mixture is stirred for 12 h and then poured into 1.5 L of a 10% sodium hydrogen carbonate solution. The aqueous phase is extracted with dichloromethane. The combined organic phases are dried over $Na_2SO_4$ and evaporated down.

Yield: 143.4 g of a compound Z2a (colourless oil)

66.0 g of the compound Z2a are placed in 500 mL water and combined with 85.0 g (0.44 mol) 2,4-dichloro-5-nitropyrimidine in 500 mL diethyl ether. At −5° C. 100 mL 10% potassium hydrogen carbonate solution are added dropwise and the reaction mixture is stirred for 48 h at ambient temperature. The aqueous phase is extracted with diethyl ether, the combined organic phases are dried over $Na_2SO_4$ and evaporated down. The dark red solid is extracted with petroleum ether and suction filtered.

Yield: 88.0 g of a compound Z2b (yellow crystals)

88.0 g of the compound Z2b are dissolved in 1000 mL glacial acetic acid and at 60° C. 85 g iron powder are added batchwise, while the temperature rises to 110° C. The mixture is stirred for 1 h at 60° C., then suction filtered hot through cellulose and evaporated down. The brown solid is stirred with 700 mL water and suction filtered.

Yield: 53.3 g of a compound Z2c (light brown crystals)

53.3 g of the compound Z2c are dissolved in 300 mL dimethylacetamide and combined with 13 mL (0.21 mol) methyl iodide. At −5° C. 5.0 g (0.21 mol) sodium hydride are added batchwise as 60% dispersion in mineral oil. After 12 h the reaction mixture is poured onto 1000 mL ice water and the precipitate formed is suction filtered.

Yield: 40.0 g of a compound Z2d (colourless crystals)

4.0 g of the compound Z2d and 2.8 g (16 mmol) of 4-amino-3-chlorobenzoic acid are suspended in 25 mL ethanol and 60 mL water, combined with 3 mL conc. hydrochloric acid and refluxed for 43 h. The precipitate formed on cooling is suction filtered and washed with water, ethanol and diethyl ether.

Yield: 0.9 g of a compound Z2 (colourless crystals)

In order to synthesise the compounds Ex. 19, 21, 22, 23, 45, 55, 58, 116, 128, 131, 133, 134, 136, 138, 177, 217, 231, 239, 46, 184, 166 and 187 first of all an intermediate compound Z3

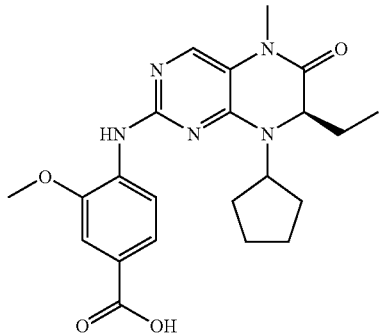

Z3 is prepared as described below.

54.0 g (0.52 mol) D-2-aminobutyric acid are suspended in 540 mL methanol and 132 g (1.1 mol) thionyl chloride are slowly added while cooling with ice. The mixture is refluxed for 1.5 h and then evaporated down. The oil remaining is combined with 540 mL tert-butylmethylether and the colourless crystals obtained are suction filtered.

Yield: 78.8 g of a compound Z3a (colourless crystals)

74.2 g of the compound Z3a and 43.5 mL (0.49 mol) cyclopentanone are dissolved in 800 mL dichloromethane. After the addition of 40.0 g (0.49 mol) sodium acetate and 150.0 g (0.71 mol) sodium triacetoxyborohydride at 0° C. the mixture is stirred for 12 h at ambient temperature and then 500 mL 20% sodium hydrogen carbonate solution are added. The aqueous phase is extracted with dichloromethane. The combined organic phases are washed with water, dried over MgSO$_4$ and evaporated down.

Yield: 85.8 g of a compound Z3b (light yellow oil)

40.0 g of the compound Z3b and 30.0 g (0.22 mol) potassium carbonate are suspended in 600 mL acetone and while cooling with ice combined with 45.0 g (0.23 mol) 2,4-dichloro-5-nitropyrimidine in 200 mL acetone. After 12 h a further 5.0 g of 2,4-dichloro-5-nitropyrimidine are added and the mixture is stirred for 3 h. The reaction mixture is evaporated down, taken up in 800 mL ethyl acetate and 600 mL water and the aqueous phase is extracted with ethyl acetate. The combined organic phases are washed with water, dried over MgSO$_4$ and evaporated down.

Yield: 75.0 g of a compound Z3c (brown oil)

100 g of the compound Z3c are dissolved in 650 mL glacial acetic acid and at 70° C. 20 g iron powder are added batchwise. The mixture is stirred for 1 h at 70° C., then for 1.5 h at 100° C. and then filtered hot through kieselguhr. The reaction mixture is evaporated down, taken up in methanol/dichloromethane, applied to silica gel and purified by Soxhlet extraction with ethyl acetate. The solvent is removed and the residue is stirred with methanol.

Yield: 30.0 g of a compound Z3d (light brown crystals)

25.0 g of the compound Z3d and 6.5 mL (0.1 mol) methyl iodide are placed in 250 mL dimethylacetamide and at −10° C. 3.8 g (0.95 mol) sodium hydride are added as a 60% dispersion in mineral oil. The mixture is stirred for 20 min. at 0° C., then 30 min. at ambient temperature and finally ice is added. The reaction mixture is evaporated down and combined with 300 mL water. The precipitate formed is suction filtered and washed with petroleum ether.

Yield: 23.0 g of a compound Z3e (colourless solid)

6.0 g of the compound Z3e and 5.1 g (31 mmol) of 4-amino-3-methoxybenzoic acid are suspended in 90 mL ethanol and 350 mL water, combined with 3.5 mL conc. hydrochloric acid and refluxed for 48 h. The reaction mixture is evaporated down, the residue is stirred with methanol/diethyl ether and the precipitate formed is suction filtered.

Yield: 6.3 g of a compound Z3 (light beige crystals)

In order to synthesise the compound Ex. 81, 82, 93, 137 first of all an intermediate compound Z4

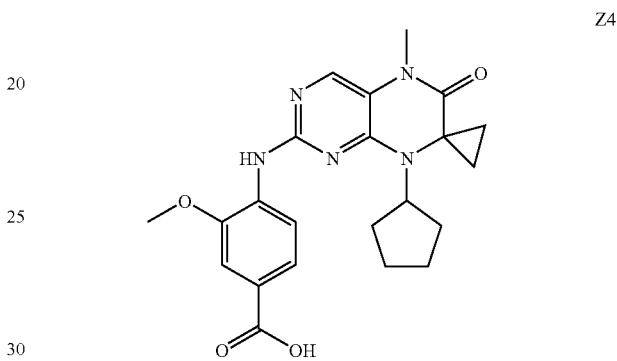

Z4 is prepared as described below.

25.0 g (0.19 mol) ethyl 1-aminocyclopropane-1-carboxylate×HCl and 16.8 g (0.20 mol) cyclopentanone are dissolved in 300 mL dichloromethane and combined with 16.4 g (0.20 mol) sodium acetate and 61.7 g (0.29 mol) sodium triacetoxyborohydride. The mixture is stirred overnight and the reaction mixture is then poured onto 400 mL 10% sodium hydrogen carbonate solution. The aqueous phase is extracted with dichloromethane. The combined organic phases are dried over Na$_2$SO$_4$ and evaporated down.

Yield: 34.5 g of a compound Z4a (colourless oil)

42.5 g (0.22 mol) 2,4-dichloro-5-nitropyrimidine in 350 mL diethyl ether are added to a mixture of 34.5 g of the compound Z4a in 350 mL water. At −5° C. 80 mL 10% potassium hydrogen carbonate solution are added and the mixture is stirred overnight at ambient temperature. The aqueous phase is extracted with diethyl ether. The combined organic phases are dried over Na$_2$SO$_4$ and evaporated down.

Yield: 53.8 g of a compound Z4b (brown oil)

20.1 g of the compound Z4b are dissolved in 200 mL glacial acetic acid and at 60° C. 19.1 g of iron powder are added batchwise, while the temperature rises to 100° C. The mixture is stirred for 3 h at 60° C., then suction filtered through cellulose and evaporated down. The residue is extracted from water and ethyl acetate and the yellow precipitate is suction filtered. The filtrate is washed with dilute ammonia and water, the organic phase is dried over Na$_2$SO$_4$ and evaporated down. After the addition of diethyl ether the product crystallises out.

Yield: 4.0 g of a compound Z4c (yellow crystals)

7.8 g of the compound Z4c and 2.6 mL (0.04 mol) methyl iodide are dissolved in 100 mL dimethylacetamide and at −5° C. 1.5 g (0.04 mol) sodium hydride as a 60% dispersion in mineral oil are added batchwise. After 2 h the reaction mixture is poured onto ice water and the precipitate formed is suction filtered.

Yield: 7.5 g of a compound Z4d (light brown crystals)

3.0 g of the compound Z4d and 1.9 g (11 mmol) of 4-amino-3-methoxybenzoic acid are suspended in 40 mL ethanol and 80 mL water, combined with 2 mL conc. hydrochloric acid and refluxed for 20 h. A further 0.5 g 4-amino-3-methoxybenzoic acid is added and the mixture is refluxed for 48 h. The precipitate formed on cooling is suction filtered and washed with water, ethanol and diethyl ether.

Yield: 2.1 g of a compound Z4 (colourless crystals)

In order to synthesise the compounds Ex. 162, 43, 53, 161, 202, 211, 215 and 212 first of all an intermediate compound Z5

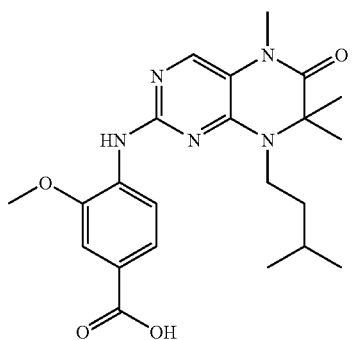

Z5 is prepared as described below.

A mixture of 73.4 mL (0.5 mol) ethyl 2-bromoisobutyrate, 87.1 mL (0.75 mol) 3-methyl-1-butylamine, 82.5 g (0.6 mol) sodium iodide and 76.0 g (0.6 mol) potassium carbonate in 1000 mL ethyl acetate is refluxed for 3 days. Any salts present are filtered off and the filtrate is evaporated down.

Yield: 97.0 g of a compound Z5a (red oil)

49.0 g (0.25 mol) 2,4-dichloro-5-nitropyrimidine and 38.3 g (0.28 mol) potassium carbonate are suspended in 500 mL acetone and at 0° C. combined with 93.0 g of the compound Z5a in 375 mL acetone. The reaction mixture is stirred overnight at ambient temperature, filtered and evaporated down. The residue dissolved in ethyl acetate is washed with water and the organic phase is dried over $MgSO_4$ and evaporated down.

Yield: 102.7 g of a compound Z5b (brown oil)

22.7 g of the compound Z5b are dissolved in 350 mL glacial acetic acid and at 60° C. 17.4 g of iron powder are added batchwise. After the addition has ended the mixture is refluxed for 0.5 h, filtered hot and evaporated down. The residue is taken up in 200 mL dichloromethane/methanol (9:1) and washed with sodium chloride solution. The organic phase is suction filtered through kieselguhr, dried over $MgSO_4$, evaporated down and purified by column chromatography (eluant: ethyl acetate/cyclohexane 1:1).

Yield: 1.9 g of a compound Z5c (colourless crystals)

1.9 g of the compound Z5c are dissolved in 32 mL dimethylacetamide and while cooling with ice combined with 0.3 g (7 mmol) of sodium hydride as a 60% dispersion in mineral oil. After 10 min. 0.5 mL (7 mmol) of methyl iodide are added and the mixture is stirred for 3 h at ambient temperature. The reaction mixture is evaporated down and combined with water. The precipitate formed is suction filtered and washed with petroleum ether.

Yield: 1.6 g of a compound Z5d (colourless crystals)

14.0 g of the compound Z5d and 10.0 g (0.06 mol) 4-amino-3-methoxybenzoic acid are suspended in 200 mL dioxane and 80 mL water, combined with 10 mL conc. hydrochloric acid and refluxed for 40 h. The precipitate formed on cooling is suction filtered and washed with water, dioxane and diethyl ether.

Yield: 13.9 g of a compound Z5 (colourless crystals)

In order to synthesise the compounds Ex. 88, 194, 229 and 89 first of all an intermediate compound Z6

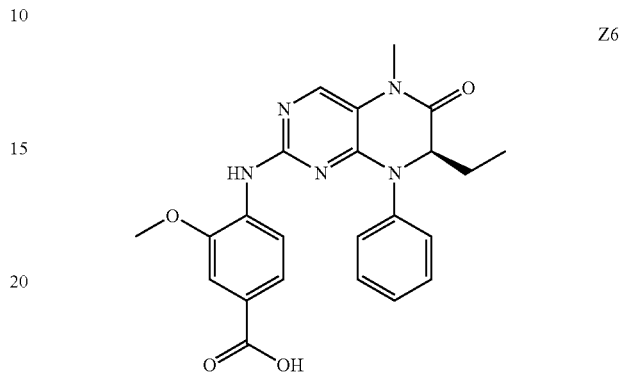

Z6 is prepared as described below.

6.0 g (0.06 mol) L-2-aminobutyric acid is placed in 80 mL of 0.5 M sulphuric acid and at 0° C. combined with 5.5 g (0.08 mol) sodium nitrite in 15 mL water. The reaction mixture is stirred for 22 h at 0° C., combined with ammonium sulphate and filtered. The filtrate is extracted with diethyl ether and the combined organic phase is dried over $MgSO_4$ and evaporated down.

Yield: 6.0 g of a compound Z6a (yellow oil)

200 mL methanol are combined successively with 65.0 mL (0.89 mol) thionyl chloride and 76.0 g of the compound Z6a in 50 mL methanol while cooling with ice. The mixture is stirred for 1 h at 0° C. and 2 h at ambient temperature and then the methanol and remaining thionyl chloride are eliminated in vacuo at 0° C.

Yield: 40.0 g of a compound Z6b (yellow oil)

30.0 mL (0.17 mol) trifluoromethanesulphonic acid anhydride are placed in 150 mL dichloromethane and while cooling with ice combined with a solution of 20.0 g of the compound Z6b and 14.0 mL (0.17 mol) pyridine in 50 mL dichloromethane within one hour. The mixture is stirred for 2 h at ambient temperature, any salts formed are suction filtered and then washed with 100 mL water. The organic phase is dried over $MgSO_4$ and evaporated down.

Yield: 42.0 g of a compound Z6c (bright yellow oil)

42.0 g of the compound Z6c in 200 mL dichloromethane is added dropwise to a solution of 15.5 mL (0.17 mol) aniline and 24.0 mL (0.17 mol) triethylamine in 400 mL dichloromethane within one hour while cooling with ice. The mixture is stirred for 1 h at ambient temperature and for a further 2 h at 35° C. The reaction mixture is washed with water, dried over $MgSO_4$ and evaporated down. The residue remaining is purified by distillation (95-100° C., $1*10^{-3}$ mbar).

Yield: 14.0 of a compound Z6d (colourless oil)

14.0 g of the compound Z6d and 16.0 g (0.1 mol) potassium carbonate are suspended in 100 mL acetone and at 10° C. combined with 16.0 g (0.08 mol) 2,4-dichloro-5-nitropyrimidine. The mixture is stirred for 4 h at 40° C., any salts formed are suction filtered and the filtrate is evaporated down.

The residue is taken up in 300 mL ethyl acetate and washed with water. The organic phase is dried over MgSO$_4$ and evaporated down.

Yield: 31.0 g of a compound Z6e (brown oil)

31.0 g of the compound Z6e are dissolved in 200 mL glacial acetic acid and at 60° C. 10 g of iron powder are added batchwise, while the temperature rises to 85° C. The mixture is stirred for a further hour at 60° C., filtered through kieselguhr and evaporated down. The residue is extracted with methanol.

Yield: 4.5 g of a compound Z6f (brown crystals)

0.6 g (16 mmol) of sodium hydride as a 60% dispersion in mineral oil are added batchwise at −20° C. to a mixture of 4.5 g of the compound Z6f and 1.0 mL (16 mmol) methyl iodide in 100 mL dimethylacetamide. After 1 h the reaction mixture is combined with 50 mL water and evaporated down. The residue is stirred with 200 mL water, the precipitate is suction filtered and washed with petroleum ether.

Yield: 4.5 g of a compound Z6g (colourless crystals)

A suspension of 1.5 g of the compound Z6g and 1.4 g (8 mmol) of methyl 4-amino-3-methoxybenzoate in 30 mL toluene is combined with 0.4 g (0.6 mmol) of 2,2'-bis-(diphenylphosphino)-1,1'-binaphthyl, 0.23 g (0.3 mmol) of tris(dibenzylideneacetone)-dipalladium(0) and 7.0 g (21 mmol) of caesium carbonate and refluxed for 17 h. The reaction mixture is applied to silica gel and purified by column chromatography (eluant: dichloromethane/methanol 9:1).

Yield: 1.7 g of a compound Z6h (yellow crystals)

1.7 g of the compound Z6h are dissolved in 50 mL dioxane, combined with 15 mL semiconc. hydrochloric acid and refluxed for 12 h. After cooling the precipitate formed is suction filtered.

Yield: 1.1 g of a compound Z6 (colourless solid)

In order to synthesise the compound Ex. 26, 20, 32, 56, 101, 112, 209 first of all an intermediate compound Z7

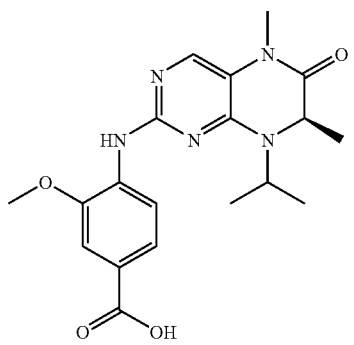

is prepared as described below.

50.0 g (0.36 mol) D-alaninemethylester×HCl is suspended in 500 mL dichloromethane and 35 mL acetone and combined with 30.0 g (0.37 mol) sodium acetate and 80.0 g (0.38 mol) sodium triacetoxyborohydride. The mixture is stirred for 12 h and then poured onto 400 mL 10% sodium hydrogen carbonate solution. The organic phase is dried over Na$_2$SO$_4$ and evaporated down.

Yield: 51.0 g of a compound Z7a (yellow oil)

A suspension of 51.0 g of the compound Z7a in 450 mL water is combined with 80.0 g (0.41 mol) 2,4-dichloro-5-nitropyridine in 450 mL diethyl ether. At −5° C. 100 mL 10% potassium hydrogen carbonate solution are added dropwise. The reaction mixture is stirred for 3 h, the organic phase is dried over Na$_2$SO$_4$ and evaporated down.

Yield: 74 g of a compound Z7b (yellow oil)

18.6 g of the compound Z7b are dissolved in 200 mL glacial acetic acid and at 60° C. 20.0 g of iron powder are added batchwise. The mixture is stirred for 2 h at 60° C. and then suction filtered through cellulose. The residue is dissolved in ethyl acetate and washed with water and conc. ammonia. The organic phase is dried over Na$_2$SO$_4$ and evaporated down. The residue is crystallised from diethyl ether.

Yield: 9.8 g of a compound Z7c (colourless crystals)

17.0 g of the compound Z7c and 7 mL (0.1 mol) methyl iodide are dissolved in 200 mL dimethylacetamide and at −5° C. combined with 4.0 g (0.1 mol) sodium hydride as a 60% dispersion in mineral oil. The reaction mixture is stirred for 30 min. and then poured onto 300 mL ice water. The precipitate formed is suction filtered and extracted with petroleum ether.

Yield: 14.8 g of a compound Z7d (beige crystals)

0.9 g of the compound Z7d and 1.5 g (9 mmol) of 4-amino-3-methoxybenzoic acid are heated to 210° C. for 30 min. After cooling the residue is extracted with ethyl acetate and the precipitate obtained is suction filtered.

Yield: 1.2 g of a compound Z7 (grey crystals)

The following acids are prepared, for example, analogously to the syntheses described.

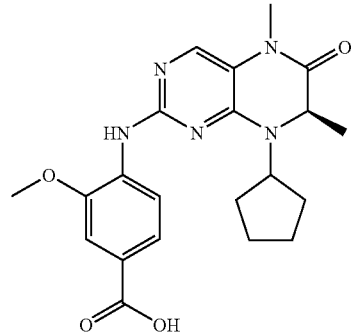

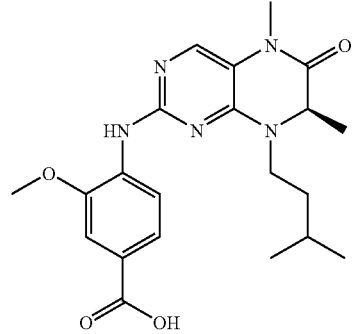

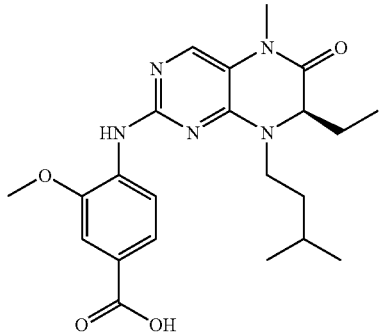

-continued

Z11

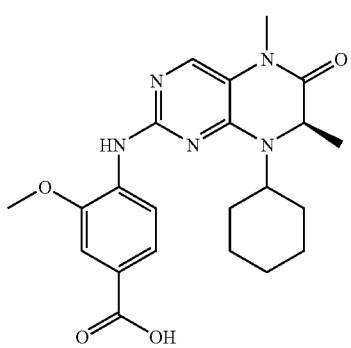

Synthesis of the Amine Components L-R5

The following amines are obtained as follows.

1,1-dimethyl-2-dimethylamino-1-yl-ethylamine and
1,1-dimethyl-2-piperidin-1-yl-ethylamine

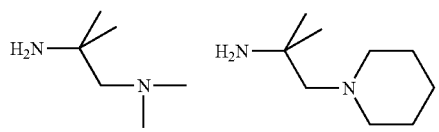

The compounds are prepared according to the following references: (a) S. Schuetz et al. *Arzneimittel-Forschung* 1971, 21, 739-763, (b) V. M. Belikov et al. *Tetrahedron* 1970, 26, 1199-1216 and (c) E. B. Butler and McMillan *J. Amer. Chem. Soc.* 1950, 72, 2978.

Other amines are prepared in a modified manner from that described in the above literature, as follows.

1,1-dimethyl-2-morpholin-1-yl-ethylamine

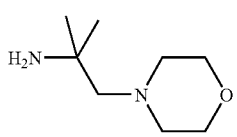

8.7 mL morpholine and 9.3 mL 2-nitropropane are taken, and cooled with ice, 7.5 mL formaldehyde (37%) and 4 mL of a 0.5 mol/L NaOH solution are slowly added dropwise (<10° C.). Then the mixture is stirred for 1 h at 25° C. and 1 h at 50° C. The solution is treated with water and ether and the aqueous phase is extracted 3× with ether. The combined org. phase is dried over $NaSO_4$ and combined with HCl in dioxane (4 mol/l), the precipitate formed is suction filtered.

Yield: 21.7 g white powder.

5 g of the white powder are dissolved in 80 mL methanol and with the addition of 2 g RaNi treated with hydrogen at 35° C. and 50 psi for 40 minutes. This yielded 3.6 g of 1,1-dimethyl-2-morpholin-1-yl-ethylamine.

The following amines are prepared analogously to this method.

1,1-dimethyl-N-methylpiperazin-1-yl-ethylamine

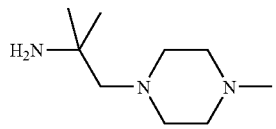

1,1-dimethyl-2-pyrrolidin-1-yl-ethylamine

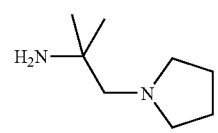

Synthesis of 1,3-dimorpholin-2-amino-propane

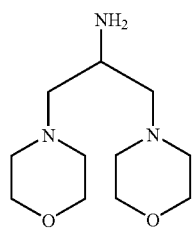 [SMILES: NC(CN1CCOCC1)CN1CCOCC1]

5 g of 1,3-dimorpholin-2-nitropropane made by Aldrich is dissolved in 80 mL methanol and with the addition of 2 g RaNi treated with hydrogen at 30° C. and 50 psi for 5.5 h. 4.2 g of 1,3-dimorpholin-2-amino-propane was obtained.

4-aminobenzylmorpholine

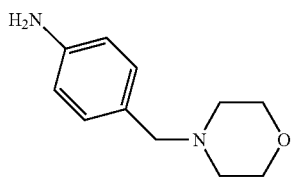 [SMILES: Nc1ccc(CN2CCOCC2)cc1]

The preparation of this amine is described in the following reference:

S. Mitsuru et al. *J. Med. Chem.* 2000, 43, 2049-2063

4-amino-1-tetrahydro-4H-pyran-4-yl-piperidine

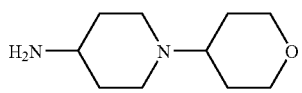

20 g (100 mmol) of 4-tert-butyloxycarbonyl-aminopiperidine are dissolved in 250 mL $CH_2Cl_2$ and stirred for 12 h at RT with 10 g (100 mmol) of tetrahydro-4H-pyran-4-one and 42 g (200 mmol) of $NaBH(OAc)_3$. Then the mixture is combined with water and potassium carbonate, the org. phase is separated off and dried and the solvent is eliminated in vacuo. The residue is dissolved in 200 mL CH$_2$Cl$_2$ and stirred for 12 h at RT with 100 mL trifluoroacetic acid. The solvent is eliminated in vacuo, the residue is taken up in CHCl$_3$ and again concentrated by evaporation, then taken up in acetone and the hydrochloride is precipitated with ethereal HCl. Yield: 14.3 g (56%).

cis- and trans-4-morpholino-cyclohexylamine

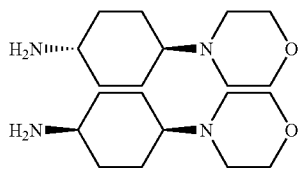

dibenzyl-4-morpholino-cyclohexylamine 3.9 g (30 mmol) of) 4-dibenzylcyclohexanone are dissolved in 100 mL CH$_2$Cl$_2$ and stirred with 3.9 g (45 mmol) of morpholine and 9.5 g (45 mmol) of NaBH(OAc)$_3$ for 12 h at RT. Then the mixture is combined with water and potassium carbonate, the org. phase is separated off, dried and the solvent is eliminated in vacuo. The residue is purified through a silica gel column (approx 20 mL silica gel; approx 500 mL ethyl acetate 90/methanol 10+1% conc. ammonia). The desired fractions are evaporated down in vacuo.

Yield 6.6 g (60%) cis-isomer and 2 g (18%) trans-isomer.

Alternatively the trans-dibenzyl-4-morpholino-cyclohexylamine may be prepared as follows:

33 g (112 mmol) of 4-dibenzylcyclohexanone are dissolved in 300 mL MeOH, combined with 17.4 g (250 mmol) of hydroxylamine hydrochloride and stirred for 4 h at 60° C. The solvent is evaporated down in vacuo, combined with 500 mL water and 50 g potassium carbonate and extracted twice with 300 mL dichloromethane. The org. phase is dried, evaporated down in vacuo, the residue is crystallised from petroleum ether, dissolved in 1.5 L EtOH and heated to 70° C. 166 g sodium are added batchwise and the mixture is refluxed until the sodium is dissolved. The solvent is eliminated in vacuo, the residue is combined with 100 mL water and extracted twice with 400 mL ether. The org. phase is washed with water, dried, evaporated down in vacuo and the trans-isomer is isolated using a column (approx. 1.5 L silica gel; approx. 2 L ethyl acetate 80/methanol 20+2% conc. ammonia).

Yield: 12.6 g (41.2%).

6.8 g (23 mmol) of trans-1-amino-4-dibenzylaminocyclohexane is dissolved in 90 mL DMF and stirred with 5 mL (42 mmol) of 2,2'-dichloroethylether and 5 g potassium carbonate for 8 h at 100° C. After cooling the mixture is combined with 30 mL water, the crystals precipitated are suction filtered and purified through a short column (approx. 20 mL silica gel, approx. 100 mL ethyl acetate). The residue is crystallised from methanol and conc. HCl as the dihydrochloride. Yield: 7.3 g (72.4%).

trans-4-morpholino-cyclohexylamine 7.2 g (16.4 mmol) of trans-dibenzyl-4-morpholino-cyclohexylamine are dissolved in 100 mL MeOH and hydrogenated on 1.4 g Pd/C (10%) at 30-50° C. The solvent is eliminated in vacuo and the residue is crystallised from ethanol and conc. HCl.

Yield: 3.9 g (93%).

The cis-isomer may be prepared analogously.

cis- and trans-4-piperidino-cyclohexylamine

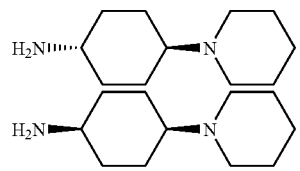

trans-dibenzyl-4-piperidino-cyclohexylamine 2.0 g (6.8 mmol) of trans-1-amino-4-dibenzylaminocyclohexane (see Ex. 2) is dissolved in 50 mL DMF and stirred for 48 h at RT with 1.6 g (7 mmol) of 1,5-dibromopentane and 2 g of potassium carbonate. The mixture is cooled, combined with water, extracted twice with 100 mL dichloromethane, dried and the solvent is eliminated in vacuo. The residue is purified through a column (approx. 100 mL silica gel, approx. 500 mL ethyl acetate 80/methanol 20+1% conc. ammonia). The desired fractions are evaporated down in vacuo and crystallised from petroleum ether. Yield: 1.2 g (49%).

trans-4-piperidino-cyclohexylamine 1.7 g (4.8 mmol) of trans-dibenzyl-4-piperidino-cyclohexylamine are dissolved in 35 mL MeOH and hydrogenated on 350 mg Pd/C (10%) at 20° C. The solvent is eliminated in vacuo and the residue is crystallised from ethanol and conc. HCl.

Yield: 1.1 g (78%).

The cis-isomer may be prepared analogously.

cis- and trans-4-(4-phenyl-piperazin-1-yl)-cyclohexylamine

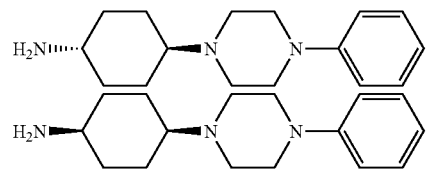

4.1 g (25.3 mmol) of 4-dibenzylcyclohexanone is dissolved in 50 mL dichloromethane and stirred with 7.4 g (25.3 mmol) of N-phenylpyperazine and 7.4 g (35 mmol) of NaBH (OAc)$_3$ for 12 h at RT. Then the mixture is combined with water and potassium carbonate, the org. phase is separated off, dried and the solvent is eliminated in vacuo. The residue is purified on a silica gel column (ethyl acetate 80/methanol 20+0.5% conc. ammonia).

Yield: 1.7 g (15.8%) cis-isomer and 0.27 (2.5%) trans-isomer.

trans-4-(4-phenyl-piperazin-1-yl)-cyclohexylamine 270 mg (0.61 mmol) of trans-dibenzyl-[4-(4-phenyl-piperazin-1-yl)-cyclohexyl]-amine are dissolved in 5 mL MeOH and hydrogenated on 40 mg Pd/C (10%) at 20-30° C. The solvent is eliminated in vacuo and the residue is crystallised from ethanol and conc. HCl.

Yield: 110 mg (69%).

The cis-isomer may be prepared analogously.

cis- and trans-4-(4-cyclopropylmethyl-piperazin-1-yl)-cyclohexylamine

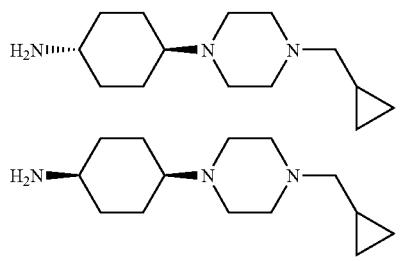

9.8 g (33.4 mmol) of 4-dibenzylcyclohexanone is dissolved in 100 mL dichloromethane and stirred with 5.6 g (40 mmol) of N-cyclopropylmethylpiperazine and 8.5 g (40 mmol) of NaBH(OAc)$_3$ for 12 h at RT. Then the mixture is combined with water and potassium carbonate, the org. phase is separated off and dried and the solvent is eliminated in vacuo. The residue is purified on a silica gel column (approx. 50 mL silica gel, approx. 3 L ethyl acetate 95/methanol 5+0.25% conc. ammonia). The desired fractions are evaporated down in vacuo. The faster eluting cis compound crystallises from ethyl acetate. The trans compound is crystallised from ethanol+conc. HCl.

Yield: 8.5 g (61%) cis-isomer and 2.2 g (13%) trans-isomer.

cis-4-(4-cyclopropylmethyl-piperazin-1-yl)-cyclohexylamine 8.5 g (20 mmol) of cis-dibenzyl-[4-(4-cyclopropylmethyl-piperazin-1-yl)-cyclohexyl]-amine are dissolved in 170 mL MeOH and hydrogenated on 1.7 g Pd/C (10%) at 30-50° C. The solvent is eliminated in vacuo and the residue is crystallised from ethanol and conc. HCl.

Yield: 4.4 g (91%).

The trans-isomer may be prepared analogously.

SYNTHESIS OF THE EXAMPLES

Example 152

0.15 g of the compound Z10, 0.14 g TBTU, 0.13 mL DIPEA are dissolved in dichloromethane and stirred for 20 minutes at 25° C. Then 90 µL 1-(3-aminopropyl)-4-methylpiperazine are added and the mixture is stirred for a further 2 hours at 25° C. The solution is then diluted with dichloromethane and extracted with water. The product is precipitated by the addition of petroleum ether, ether and ethyl acetate to the organic phase. Yield: 0.16 g of beige solid Example 164

0.10 g of the compound Z10, 0.1 g TBTU, 0.08 mL DIPEA are dissolved in 4 mL dichloromethane and stirred for 20 minutes at 25° C. Then 44 µL dimethylaminopropylamine are added and the mixture is stirred for a further 2 hours at 25° C. The solution is then diluted with dichloromethane and extracted with water. The product is precipitated by the addition of petroleum ether, ether and acetone to the organic phase. Yield: 0.08 g yellow solid.

Example 242

0.15 g of the compound Z10, 0.14 g TBTU, 0.13 mL DIPEA are dissolved in 5 mL dichloromethane and stirred for 20 minutes at 25° C. Then 75 µL 1-(2-aminoethyl)piperidine are added and the mixture is stirred for a further 2 hours at 25° C. The solution is then diluted with dichloromethane and extracted with water. The product is precipitated by the addition of petroleum ether, ether and ethyl acetate to the organic phase. Yield: 0.14 g yellow solid.

Example 188

0.1 g of the compound Z2, 0.09 g TBTU, 0.05 mL DIPEA are dissolved in 15 mL dichloromethane and stirred for 20 minutes at 25° C. Then 33 mg 1-methyl-4-aminopiperidine are added and the mixture is stirred for a further 3 hours at 25° C. The solution is extracted with 20 mL water, then evaporated down in vacuo. The product is crystallised from ether. Yield: 0.047 g white crystals.

Example 203

0.1 g of the compound Z2, 0.09 g TBTU, 0.5 mL DIPEA are dissolved in 15 mL dichloromethane and stirred for 30 minutes at 25° C. Then 50 mg 4-amino-1-benzylpiperidine are added and the mixture is stirred for a further 3 hours at 25° C. The solution is extracted with 20 mL water, then evaporated down in vacuo. The residue is then chromatographed on silica gel and the product isolated is crystallised from ether. Yield: 0.015 g white crystals.

Example 94

0.17 g of the compound Z1, 0.19 g TBTU, 0.11 mL DIPEA are dissolved in 50 mL dichloromethane and stirred for 30 minutes at 25° C. Then 63 mg 1-methyl-4-aminopiperidine are added and the mixture is stirred for a further 17 hours at 25° C. 50 mL water and 1 g potassium carbonate are added to the solution and the organic phase is separated off using a phase separation cartridge, then evaporated down in vacuo. The product is then purified by chromatography on silica gel and the purified product is crystallised using ether. Yield: 0.1 g white crystals.

Example 95

0.17 g of the compound Z1, 0.19 g TBTU, 0.11 mL DIPEA are dissolved in 50 mL dichloromethane and stirred for 30 minutes at 25° C. Then 77 mg exo-3-β-amino-tropane are added and the mixture is stirred for a further 17 hours at 25° C. 50 mL water and 1 g potassium carbonate are added to the solution and the organic phase is separated off using a phase separation cartridge, then evaporated down in vacuo. The product is then purified by chromatography on silica gel and the purified product is crystallised using ether. Yield: 0.03 g white crystals.

Example 46

0.15 g of the compound Z3, 0.12 g TBTU, 0.12 mL DIPEA are dissolved in 5 mL dichloromethane and stirred for 30 minutes at 25° C. Then 50 mg 1-methyl-4-aminopiperidine are added and the mixture is stirred for a further 2.5 hours at 25° C. stirred. The solution is then extracted with water and then evaporated down. The residue is dissolved in warm ethyl acetate and crystallised using ether and petroleum ether.

Yield: 0.025 g white crystals.

Example 80

0.2 g of the compound Z8, 0.2 g TBTU, 0.1 mL DIPEA are dissolved in 10 mL dichloromethane and stirred for 30 minutes at 25° C. Then 100 mg 1-methyl-4-aminopiperidine are added and the mixture is stirred for a further 17 hours at 25° C. The solution is then extracted with a dilute potassium carbonate solution and evaporated down. The residue is crystallised using ether. Yield: 0.12 g white crystals.

Example 190

0.2 g compound Z8, 0.2 g TBTU, 0.3 mL DIPEA are dissolved in 5 mL dichloromethane and the mixture is stirred for 1 h at 25° C. Then 0.13 g 4-amino-1-benzylpiperidine is added and the mixture is stirred for a further hour at 25° C. The solution is then diluted with 10 mL methylene chloride and extracted with 20 mL water. Then the product is purified on silica gel and crystallised by means of ethyl acetate and ether.

Yield: 0.23 g of the compound Z8

0.23 g of the benzylamine Z8 are dissolved in 10 mL methanol, combined with 50 mg Pd/C and hydrogenated for 3 h at 3 bar at 25° C. By the addition of petroleum ether and ethyl acetate white crystals are obtained. These are chromatographed on silica gel and crystallised using ethyl acetate and ether.

Yield: 0.075 g white crystals.

Example 196

0.1 g compound Z10, 0.09 g TBTU, 0.3 mL DIPEA are dissolved in 4 mL dichloromethane and stirred for 20 minutes at 25° C. Then 67 mg 1,1-dimethyl-N-methylpiperazin-1-yl-ethylamine is added and the mixture is stirred for a further 2 hours at 25° C. The solution is then diluted with dichloromethane and extracted with water. It is then chromatographed on silica gel and the residue is dissolved in acetone, combined with ethereal HCl and the precipitate formed is isolated.

Yield: 0.09 g bright yellow solid

Example 166

0.1 g of the compound Z10, 0.11 g TBTU, 0.14 mL DIPEA are dissolved in 2 mL dimethylformamide and stirred for 3 h at 50° C. Then 55 mg of 4-morpholinomethylphenylamine is added. Then the reaction is cooled to ambient temperature within 17 h. Then the dimethylformamide is eliminated in vacuo, the residue is taken up in dichloromethane and extracted with water. It is then chromatographed on silica gel and the product is crystallised from ethyl acetate and ether.

Yield: 0.06 g yellowish crystals

Example 81

0.2 g of the compound Z4, 0.2 g TBTU, 0.1 mL DIPEA are dissolved in 10 mL dichloromethane and stirred for 30 minutes at 25° C. Then 0.1 g 1-methyl-4-aminopiperidine are added and the mixture is stirred for a further 17 hours at 25° C. The solution is then extracted with aqueous potassium carbonate solution and then evaporated down. The product is crystallised using ether.

Yield: 0.16 g white crystals.

Example 162

0.1 g of the compound Z5, 0.07 g TBTU, 0.15 mL DIPEA are dissolved in 5 mL dichloromethane and stirred for 20 minutes at 25° C. Then 0.04 g 1-methyl-4-aminopiperidine are added and the mixture is stirred for a further 2 hours at 25° C. The solution is then diluted with 15 mL dichloromethane and extracted with 20 mL water. The residue is dissolved in MeOH and acetone, combined with 1 mL ethereal HCl and evaporated down. Using ether, ethyl acetate and a little MeOH a crystalline product is obtained.

Yield: 0.1 g white crystals.

Example 88

0.1 g of the compound Z6, 0.12 g TBTU, 0.12 mL DIPEA are dissolved in 10 mL dichloromethane and stirred for 30 minutes at 25° C. Then 0.04 g 1-methyl-4-aminopiperidine are added and the mixture is stirred for a further 2 hours at 25° C. The solution is then diluted with 10 mL dichloromethane and extracted with 10 mL water. Using ethyl acetate, ether and petroleum ether a crystalline product is obtained.

Yield: 0.6 g white crystals.

Example 89

0.1 g of the compound Z6, 0.08 g TBTU, 0.08 mL DIPEA are dissolved in 10 mL dichloromethane and stirred for 30 minutes at 25° C. Then 37 µL of N,N-dimethylneopentanediamine are added and the mixture is stirred for a further 2 hours at 25° C. The solution is then diluted with 10 mL dichloromethane and extracted with 10 mL water. The product is then chromatographed on silica gel and crystallised using ethyl acetate, ether and petroleum ether.

Yield: 0.005 g white crystals.

Example 26

0.15 g of the compound Z7, 0.16 g TBTU, 1 mL DIPEA are dissolved in 5 mL dichloromethane and stirred for 30 minutes at 25° C. Then 0.1 g of 4-morpholinocyclohexylamine are added and the mixture is stirred for a further 17 hours at 25° C. The residue is then combined with 10 mL 10% potassium carbonate solution, the precipitate is isolated and washed with water. Then it is dissolved in dichloromethane and again evaporated down. The product is crystallised using ethyl acetate.

Yield: 0.1 g white crystals.

Example 9

150 mg of the compound Z9 and 93 mg of cis-4-morpholino-cyclohexamine are dissolved in 5 mL dichloromethane and stirred with 160 mg TBTU and 1 mL DIPEA for 12 h at RT. The solvent is eliminated in vacuo, the residue is combined with 10 mL 10% potassium carbonate solution. The precipitate is suction filtered, washed with water, taken up in dichloromethane, dried and the solvent is eliminated in vacuo. The residue is crystallised from ethyl acetate.

Yield: 82.0 mg.

Example 16

150 mg of the compound Z8 and 73 mg trans-4-piperidino-cyclohexylamine are dissolved in 5 mL dichloromethane and stirred with 160 mg (0.50 mmol) of TBTU and 1 mL DIPEA for 12 h at RT. The solvent is eliminated in vacuo, the residue is combined with 10 mL 10% potassium carbonate solution. The precipitate is suction filtered, washed with water, taken up in dichloromethane, dried and the solvent is eliminated in vacuo. The residue is crystallised from ethyl acetate. Yield: 87.0 mg.

Example 37

100 mg of the compound Z9 and 42 mg of 3-amino-1-ethyl-pyrrolidine are dissolved in 10 mL dichloromethane and stirred with 90 mg of TBTU and 0.5 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent is eliminated in vacuo. The residue is crystallised from ethyl acetate/petroleum ether. Yield: 24.0 mg.

Example 120

100 mg of the compound Z11 and 73 mg of 4-amino-1-tetrahydro-4H-pyran-4-yl-piperidine are dissolved in 10 mL dichloromethane and this is stirred with 90 mg of TBTU and 0.5 mL DIPEA for 1 h at RT. The solvent is eliminated in vacuo, the residue is combined with 10 mL 10% potassium carbonate solution. The precipitate is suction filtered, washed with water, taken up in dichloromethane, dried and the solvent is eliminated in vacuo. The residue is crystallised from ethyl acetate/petroleum ether.

Yield: 89 mg.

Example 212

150 mg of the compound Z5 and 150 mg of trans-4-(4-cyclopropylmethyl-piperazin-1-yl)-cyclohexylamine (as the hydrochloride) are dissolved in 5 mL dichloromethane and stirred with 160 mg of TBTU and 2 mL DIPEA for 2 h at RT. The solvent is eliminated in vacuo, the residue is combined with 10 mL 10% potassium carbonate solution. The precipitate is suction filtered, washed with water, taken up in dichloromethane, dried and the solvent is eliminated in vacuo. The residue is purified through a column (20 mL silica gel, 300 mL ethyl acetate 90/methanol 10+2% conc. ammonia). The desired fractions are evaporated down in vacuo and crystallised from ethyl acetate.

Yield: 140 mg.

Example 232

390 mg of the compound Z11 and 240 mg trans-4-(4-t-butyloxycarbonyl-piperazin-1-yl)-cyclohexylamine are dissolved in 2.5 mL NMP and stirred with 482 mg of TBTU and 1 mL triethylamine for 2 h at RT. Then the mixture is combined with 100 mL water and 200 mg potassium carbonate, the precipitate is suction filtered, washed with water and purified through a silica gel column. The suitable fractions are evaporated down in vacuo, dissolved in 2 mL dichloromethane, combined with 2 mL trifluoroacetic acid and stirred for 2 h at RT, again combined with 100 ml water and 200 mg potassium carbonate and the precipitate is suction filtered and washed with water. Then the precipitate is purified through a silica gel column. The desired fractions are evaporated down in vacuo and the residue is crystallised from ethanol and conc. hydrochloric acid.

Yield: 95 mg.

Example 213

60 mg of the compound Example 232 is dissolved in 10 mL ethyl acetate and stirred with 1 mL acetic anhydride and 1 mL triethylamine for 30 min. at RT. The solvent is eliminated in vacuo, the residue is combined with water and ammonia, the precipitated crystals are suction filtered and washed with water and a little cold acetone.

Yield: 40 mg.

Example 218

1.2 g of the compound Z9 and 0.5 g of 1,4-dioxaspiro[4.5]dec-8-ylamine are dissolved in 20 mL dichloromethane and stirred with 1.28 g TBTU and 4 mL triethylamine for 12 h at RT. Then 50 mL water and 0.5 g potassium carbonate are added, the org. phase is separated off, dried and evaporated down in vacuo. The residue is crystallised from ethyl acetate, combined with 25 mL 1 N hydrochloric acid and 20 mL methanol and stirred for 30 min. at 50° C. The methanol is eliminated in vacuo, the precipitate is suction filtered, washed with water and dried. The residue is taken up in 20 mL dichloromethane and stirred with 0.5 g thiomorpholine and 0.5 g NaBH(OAc)$_3$ for 12 h at RT. Then the mixture is combined with water and potassium carbonate, the org. phase is separated off, dried and the solvent is eliminated in vacuo. The residue is purified on a silica gel column. The desired fractions are evaporated down in vacuo and the hydrochloride is precipitated with ethereal HCl.

Yield: 86 mg trans-isomer; amorphous powder.

Example 187

200 mg of the compound Z3 in 5 mL dichloromethane is combined with 0.1 mL diisopropylethylamine and 180 mg TBTU and stirred for 30 min. Then 191 mg of 4-(4-methyl-piperazin-1-yl)-phenylamine are added and the mixture is stirred overnight. The reaction mixture is combined with water and the aqueous phase is extracted with dichloromethane. The combined organic phases are dried over Na$_2$SO$_4$ and evaporated down. The residue is purified by column chromatography (eluant: dichloromethane/methanol 100:7).

Yield: 128 mg (light yellow crystals)

The compounds of formula (I) listed in Table 1 may be obtained inter alia analogously to the method described hereinbefore.

The abbreviations $X_1, X_2, X_3, X_4$ and $X_5$ used in Table 1 in each case denote a link to a position in the general formula listed in the Table instead of the corresponding groups $R^1, R^2, R^3, R^4$ and L-R$^5$.

TABLE 1

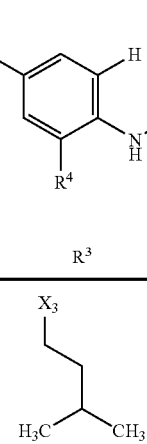

| Ex. | R¹ | R² | Config. R¹ or R² | R³ | R⁴ | $L_n$—$R^5{}_m$ |
|---|---|---|---|---|---|---|
| 1 | H | $X_2$◂CH₃ | R | $X_3$–CH₂CH(CH₃)₂ (isobutyl with extra CH₂) | $X_4$—O—CH₃ | $X_5$-(2,2,6,6-tetramethyl-1-methylpiperidin-4-yl) |
| 2 | H | $X_2$◂CH₃ | R | $X_3$-isopentyl | $X_4$—O—CH₃ | $X_5$-(1-isopropylpiperidin-4-yl) |
| 3 | H | $X_2$◂CH₃ | R | $X_3$-isopentyl | H | $X_5$-(2,2,6,6-tetramethyl-1-methylpiperidin-4-yl) |
| 4 | H | $X_2$◂CH₃ | R | $X_3$-isopentyl | H | $X_5$-(1-ethylpiperidin-4-yl) |
| 5 | H | $X_2$◂CH₃ | R | $X_3$-neopentyl | $X_4$—O—CH₃ | $X_5$-(2,2,6,6-tetramethyl-1-methylpiperidin-4-yl) |
| 6 | H | $X_2$◂CH₃ | R | $X_3$-neopentyl | $X_4$—O—CH₃ | $X_5$-(1-ethylpiperidin-4-yl) |
| 7 | H | $X_2$◂CH₃ | R | $X_3$-neopentyl | $X_4$—O—CH₃ | $X_5$-(1-isopropylpiperidin-4-yl) |

TABLE 1-continued
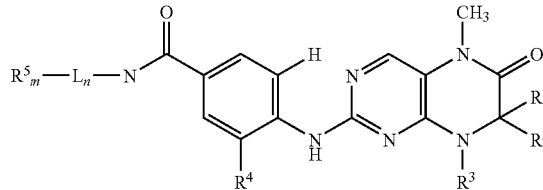
| Ex. | R¹ | R² | Config. R¹ or R² | R³ | R⁴ | Lₙ—R⁵ₘ |
|---|---|---|---|---|---|---|
| 8 | H | X₂◂CH₃ | R |  | H | 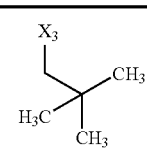 |
| 9 | H | X₂◂CH₃ | R | 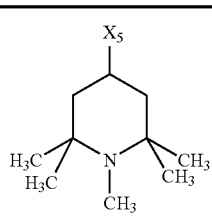 |  | 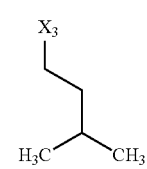 |
| 10 | H | X₂◂CH₃ | R | 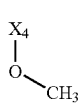 | H | 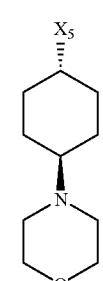 |
| 11 | H | X₂◂CH₃ | R |  | H | 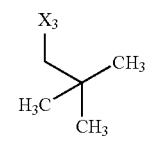 |
| 12 | H | X₂◂CH₃ | R | 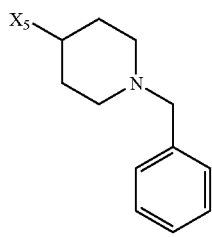 | H |  |
| 13 | H | X₂◂CH₃ | R | 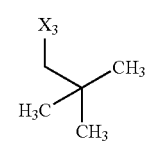 | 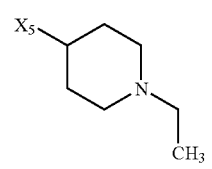 |  |

TABLE 1-continued

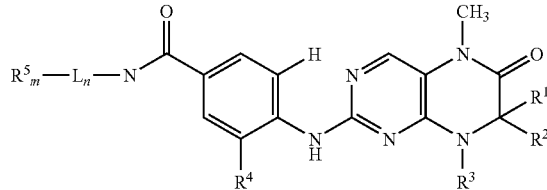

| Ex. | $R^1$ | $R^2$ | Config. $R^1$ or $R^2$ | $R^3$ | $R^4$ | $L_n-R^5_m$ |
|---|---|---|---|---|---|---|
| 14 | H | $X_2$—CH$_3$ | R | $X_3$-cyclopentyl | H | $X_5$-(1-isopropylpiperidin-4-yl) |
| 15 | H | $X_2$—CH$_3$ | R | $X_3$-cyclopentyl | $X_4$—O—CH$_3$ | $X_5$-(4-pyrrolidin-1-yl-cyclohexyl) |
| 16 | H | $X_2$—CH$_3$ | R | $X_3$-cyclopentyl | $X_4$—O—CH$_3$ | $X_5$-(4-piperidin-1-yl-cyclohexyl) |
| 17 | H | $X_2$—CH$_3$ | R | $X_3$-cyclopentyl | CH$_3$—O—$X_4$ | $X_5$-(1-ethylpiperidin-4-yl) |
| 18 | H | $X_2$—CH$_3$ | R | $X_3$-cyclopentyl | H | $X_5$-(1-ethylpiperidin-4-yl) |

TABLE 1-continued

| Ex. | R¹ | R² | Config. R¹ or R² | R³ | R⁴ | Lₙ—R⁵ₘ |
|---|---|---|---|---|---|---|
| 19 | H | X₂–CH₃ | R | cyclopentyl (X₃) | X₄–O–CH₃ | 4-pyrrolidin-1-yl-cyclohexyl (X₅, trans) |
| 20 | H | X₂◂CH₃ | R | isopropyl (X₃) | CH₃–O–X₄ | 1-ethyl-piperidin-4-yl (X₅) |
| 21 | H | X₂–CH₃ | R | cyclopentyl (X₃) | CH₃–O–X₄ | 1,2,2,6,6-pentamethyl-piperidin-4-yl (X₅) |
| 22 | H | X₂–CH₃ | R | cyclopentyl (X₃) | CH₃–O–X₄ | 1-ethyl-piperidin-4-yl (X₅) |
| 23 | H | X₂–CH₃ | R | cyclopentyl (X₃) | CH₃–O–X₄ | 1-isopropyl-piperidin-4-yl (X₅) |

TABLE 1-continued

| Ex. | R¹ | R² | Config. R¹ or R² | R³ | R⁴ | Lₙ—R⁵ₘ |
|---|---|---|---|---|---|---|
| 24 | H | X₂◂CH₃ | R | X₃-cyclopentyl | X₄-O-CH₃ | X₅-cyclohexyl-morpholine |
| 25 | H | X₂◂CH₃ | R | X₃-cyclopentyl | X₄-O-CH₃ | X₅-cyclohexyl-piperidine |
| 26 | H | X₂◂CH₃ | R | X₃-CH(CH₃)₂ | X₄-O-CH₃ | X₅-cyclohexyl-morpholine |
| 27 | H | X₂—CH₃ | R | X₃-CH(CH₃)₂ | X₄-O-CH₃ | X₅-cyclohexyl-morpholine |

TABLE 1-continued

| Ex. | R¹ | R² | Config. R¹ or R² | R³ | R⁴ | Lₙ—R⁵ₘ |
|---|---|---|---|---|---|---|
| 28 | H | X₂—CH₃ (ethyl) | R | X₃ isopropyl | X₄—OCH₃ | X₅-cyclohexyl-morpholine |
| 29 | H | X₂◂CH₃ | R | X₃ isobutyl (3-methylbutyl) | X₄—OCH₃ | X₅-cyclohexyl-piperidine |
| 30 | H | X₂◂CH₃ | R | X₃ cyclopentyl | CH₃—O—X₄ | X₅-1,2,2,6,6-pentamethylpiperidin-4-yl |
| 31 | H | X₂◂CH₃ | R | X₃ cyclopentyl | H | X₅-1,2,2,6,6-pentamethylpiperidin-4-yl |
| 32 | H | X₂◂CH₃ | R | X₃ isopropyl | CH₃—O—X₄ | X₅-1,2,2,6,6-pentamethylpiperidin-4-yl |

TABLE 1-continued

| Ex. | R¹ | R² | Config. R¹ or R² | R³ | R⁴ | Lₙ—R⁵ₘ |
|---|---|---|---|---|---|---|
| 33 | H | X₂⬩CH₃ | R | X₃–CH(CH₃)₂ (isobutyl) | H | X₅-(1,2,2,6,6-pentamethylpiperidin-4-yl) |
| 34 | H | X₂⬩CH₃ | R | X₃–CH₂CH(CH₃)₂ (isopentyl) | X₄–O–CH₃ | X₅-(trans-4-(pyrrolidin-1-yl)cyclohexyl) |
| 35 | H | X₂⬩CH₃ | R | X₃–CH₂CH(CH₃)₂ | X₄–O–CH₃ | X₅-(trans-4-(pyrrolidin-1-yl)cyclohexyl) |
| 36 | H | X₂⬩CH₃ | R | X₃-cyclopentyl | X₄–O–CH₃ | X₅-(trans-4-(pyrrolidin-1-yl)cyclohexyl) |
| 37 | H | X₂⬩CH₃ | R | X₃–CH₂CH(CH₃)₂ | X₄–O–CH₃ | X₅-(1-ethylpyrrolidin-3-yl) |

TABLE 1-continued

| Ex. | R¹ | R² | Config. R¹ or R² | R³ | R⁴ | Lₙ—R⁵ₘ |
|---|---|---|---|---|---|---|
| 38 | H | X₂—CH₃ | R | X₃—CH₂CH₂—CH(CH₃)₂ | X₄—O—CH₃ | X₅-cyclohexyl-N-morpholine |
| 39 | H | X₂—CH₃ | R | X₃—CH₂CH₂—CH(CH₃)₂ | H | X₅-pyrrolidine-N-ethyl |
| 40 | H | X₂—CH₃ | R | X₃-cyclopentyl | X₄—O—CH₃ | X₅-cyclohexyl-N-morpholine |
| 41 | H | X₂—CH₃ | R | X₃-phenyl | CH₃—O—X₄ | X₅-piperidine-N-CH₃ |
| 42 | H | X₂—CH₂CH₃ | R | X₃—CH₂CH₂—CH(CH₃)₂ | CH₃—O—X₄ | X₅-azabicyclo-N-CH₃ |

TABLE 1-continued

| Ex. | R¹ | R² | Config. R¹ or R² | R³ | R⁴ | L_n—R⁵_m |
|---|---|---|---|---|---|---|
| 43 | X₁—CH₃ | X₂—CH₃ | | X₃—CH₂CH₂—CH(CH₃)₂ | H₃C—O—X₄ | X₅-(8-methyl-8-azabicyclo[3.2.1]oct-3-yl) |
| 44 | H | X₂—CH₂CH₃ | R | X₃-cyclopentyl | H | X₅-(1-methylpiperidin-4-yl) |
| 45 | H | X₂—CH₂CH₃ | R | X₃-cyclopentyl | H₃C—O—X₄ | X₅-(8-methyl-8-azabicyclo[3.2.1]oct-3-yl) |
| 46 | H | X₂—CH₂CH₃ | R | X₃-cyclopentyl | H₃C—O—X₄ | X₅-(1-methylpiperidin-4-yl) |
| 47 | H | X₂—CH₂CH₃ | R | X₃-cyclopentyl | H | X₅-(8-methyl-8-azabicyclo[3.2.1]oct-3-yl) |
| 48 | H | X₂—CH₃ | R | X₃-phenyl | H | X₅-(1-methylpiperidin-4-yl) |

TABLE 1-continued

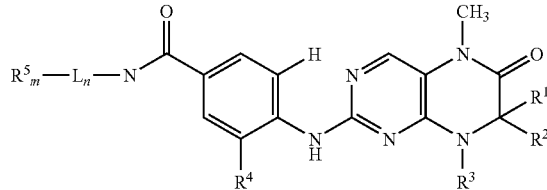

| Ex. | R¹ | R² | Config. R¹ or R² | R³ | R⁴ | $L_n-R^5_m$ |
|---|---|---|---|---|---|---|
| 49 | H | X₂—CH₃ | R | X₃–cyclopentyl | CH₃–O–X₄ | H₃C–C(CH₃)(X₅)–CH₂–pyrrolidinyl |
| 50 | H | X₂—CH₃ | R | X₃–CH₂–C(CH₃)₂–CH₃ | X₄–O–CH₃ | H₃C–C(CH₃)(X₅)–CH₂–pyrrolidinyl |
| 51 | H | X₂–cyclopropyl | R | X₃–cyclopentyl | CH₃–O–X₄ | X₅–C(CH₃)(CH₂CH₃)–CH₂–N(CH₃)₂ |
| 52 | H | X₂—CH₃ | R | X₃–CH₂–C(CH₃)₂–CH₃ | CH₃–O–X₄ | X₅–C(CH₃)(CH₂CH₃)–CH₂–N(CH₃)₂ |
| 53 | X₁—CH₃ | X₂—CH₃ | — | X₃–CH₂–CH(CH₃)–CH₃ | CH₃–O–X₄ | X₅–C(CH₃)(CH₂CH₃)–CH₂–N(CH₃)₂ |
| 54 | H | X₂–CH₂CH₃ | R | X₃–CH(CH₃)₂ | CH₃–O–X₄ | H₃C–C(CH₃)(X₅)–CH₂–pyrrolidinyl |

TABLE 1-continued

| Ex. | R¹ | R² | Config. R¹ or R² | R³ | R⁴ | Lₙ—R⁵ₘ |
|---|---|---|---|---|---|---|
| 55 | H | X₂—CH₃ (wedge) | R | cyclopentyl-X₃ | CH₃—O—X₄ | H₃C-C(CH₃)(X₅)-CH₂-N(pyrrolidine) |
| 56 | H | X₂—CH₃ (dash) | R | isopropyl-X₃ | CH₃—O—X₄ | H₃C-C(CH₃)(X₅)-CH₂-N(pyrrolidine) |
| 57 | H | X₂—CH₃ (wedge) | R | isopropyl-X₃ | CH₃—O—X₄ | H₃C-CH₂-C(CH₃)(X₅)-CH₂-N(CH₃)₂ |
| 58 | H | X₂—CH₃ (wedge) | R | cyclopentyl-X₃ | CH₃—O—X₄ | H₃C-CH₂-C(CH₃)(X₅)-CH₂-N(CH₃)₂ |
| 59 | H | X₂—CH₃ (dash) | R | phenyl-X₃ | H₃C—O—X₄ | X₅-(1-methylpiperidin-4-yl) |
| 60 | H | X₂—CH₃ (dash) | R | cyclopentyl-X₃ | CH₃—O—X₄ | H₃C-CH₂-C(CH₃)(X₅)-CH₂-N(CH₃)₂ |

TABLE 1-continued

| Ex. | R¹ | R² | Config. R¹ or R² | R³ | R⁴ | Lₙ—R⁵ₘ |
|---|---|---|---|---|---|---|
| 61 | X₁–CH₃ | X₂–CH₃ |  | X₃–CH₂CH(CH₃)CH₃ | H₃C–O–X₄ | X₅–(1-methylpiperidin-4-yl) |
| 62 | H | X₂◂CH₃ | R | X₃–cyclopentyl | CH₃–O–X₄ | (H₃C–CH₂)₂N–CH₂CH₂–X₅ |
| 63 | H | X₂◂CH₃ | R | X₃–cyclopentyl | CH₃–O–X₄ | morpholino–CH₂CH₂CH₂–X₅ |
| 64 | H | X₂◂CH₃ | R | X₃–cyclopentyl | CH₃–O–X₄ | piperidino–CH₂CH₂CH₂–X₅ |
| 65 | H | X₂◂CH₃ | R | X₃–cyclopentyl | CH₃–O–X₄ | morpholino–CH₂CH₂–X₅ |
| 66 | H | X₂◂CH₃ | R | X₃–cyclopentyl | CH₃–O–X₄ | piperidino–CH₂CH₂–X₅ |
| 67 | H | X₂◂CH₃ | R | X₃–cyclopentyl | CH₃–O–X₄ | (H₃C)₂N–CH₂CH₂–X₅ |
| 68 | H | X₂◂CH₃ | R | X₃–cyclopentyl | H | N-methyl-tropane–X₅ |
| 69 | H | X₂◂CH₃ | R | X₃–cyclopentyl | H | morpholino–CH₂CH₂CH₂–X₅ |

TABLE 1-continued

| Ex. | R¹ | R² | Config. R¹ or R² | R³ | R⁴ | Lₙ—R⁵ₘ |
|---|---|---|---|---|---|---|
| 70 | H | X₂—CH₃ (wedge) | R | X₃-cyclopentyl | H | piperidine-CH₂CH₂-X₅ |
| 71 | H | X₂-CH₃ | R | X₃-CH(CH₃)₂ | H₃C-O-X₄ | X₅-CH₂CH₂-morpholine |
| 72 | H | X₂-CH₃ | R | X₃-CH(CH₃)₂ | H₃C-O-X₄ | X₅-CH₂CH₂-piperidine |
| 73 | H | X₂-CH₃ | R | X₃-CH(CH₃)₂ | H | X₅-CH₂CH₂-N(CH₂CH₃)₂ |
| 74 | H | X₂-CH₃ | R | X₃-CH(CH₃)₂ | H₃C-O-X₄ | X₅-CH₂CH₂-N(CH₂CH₃)₂ |
| 75 | H | X₂—CH₃ (wedge) | R | X₃-cyclopentyl | CH₃-O-X₄ | H₃C-N(CH₃)-CH₂CH₂CH₂-X₅ |
| 76 | H | X₂—CH₃ (wedge) | R | X₃-cyclopentyl | CH₃-O-X₄ | H₃C-CH₂-N(CH₂CH₃)-CH₂CH₂CH₂-X₅ |
| 77 | H | X₂-CH₃ | R | X₃-CH(CH₃)₂ | H | X₅-CH₂CH₂-piperidine |

TABLE 1-continued

| Ex. | R¹ | R² | Config. R¹ or R² | R³ | R⁴ | Lₙ—R⁵ₘ |
|---|---|---|---|---|---|---|
| 78 | H | X₂–CH₃ (ethyl) | R | X₃–CH(CH₃)₂ | H | X₅–CH₂CH₂–morpholine |
| 79 | H | X₂◀CH₃ | R | X₃–cyclopentyl | H | N-methylpiperidin-4-yl–X₅ |
| 80 | H | X₂◀CH₃ | R | X₃–cyclopentyl | CH₃–O–X₄ | N-methylpiperidin-4-yl–X₅ |
| 81 | H | X₂–cyclopropyl | R | X₃–cyclopentyl | CH₃–O–X₄ | X₅–(N-methylpiperidin-4-yl) |
| 82 | H | X₂–cyclopropyl | R | X₃–cyclopentyl | CH₃–O–X₄ | X₅–(N-methyl-azabicyclic) |
| 83 | H | X₂◀CH₃ | R | X₃–cyclopentyl | H₃C–X₄ | N-methylpiperidin-4-yl–X₅ |
| 84 | H | X₂▸CH₃ | R | X₃–cyclohexyl | CH₃–O–X₄ | X₅–(N-methylpiperidin-4-yl) |

TABLE 1-continued

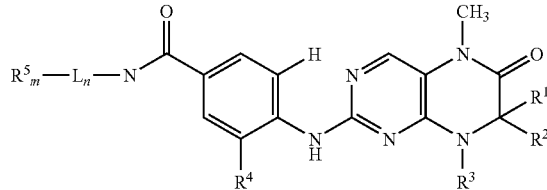

| Ex. | R¹ | R² | Config. R¹ or R² | R³ | R⁴ | $L_n$—$R^5_m$ |
|---|---|---|---|---|---|---|
| 85 | H | $X_2$▪CH₃ | R | $X_3$-cyclohexyl | H | $X_5$-(1-methylpiperidin-4-yl) |
| 86 | H | $X_2$▪CH₃ | R | $X_3$-cyclohexyl | CH₃O–$X_4$ | $X_5$-CH₂C(CH₃)(C₂H₅)CH₂N(CH₃)₂ |
| 87 | H | $X_2$▪CH₃ | R | $X_3$-cyclohexyl | CH₃O–$X_4$ | $X_5$-C(CH₃)₂CH₂-(pyrrolidin-1-yl) |
| 88 | H | $X_2$–CH₂CH₃ | R | $X_3$-phenyl | CH₃O–$X_4$ | $X_5$-(1-methylpiperidin-4-yl) |
| 89 | H | $X_2$–CH₂CH₃ | R | $X_3$-phenyl | CH₃O–$X_4$ | $X_5$-CH₂C(CH₃)(C₂H₅)CH₂N(CH₃)₂ |
| 90 | H | $X_2$–CH₂CH₃ | R | $X_3$-CH₂CH₂CH(CH₃)₂ | CH₃O–$X_4$ | $X_5$-C(CH₃)₂CH₂N(CH₃)₂ |

TABLE 1-continued

| Ex. | R¹ | R² | Config. R¹ or R² | R³ | R⁴ | Lₙ—R⁵ₘ |
|---|---|---|---|---|---|---|
| 91 | H | X₂–CH₃ | R | cyclohexyl-X₃ | CH₃–O–X₄ | X₅-(N-methyl-8-azabicyclo) |
| 92 | H | X₂–CH₃ | R | cyclohexyl-X₃ | H | X₅-(N-methyl-8-azabicyclo) |
| 93 | H | X₂-cyclopropyl | R | cyclopentyl-X₃ | H | H₃C–N-piperidinyl-X₅ |
| 94 | H | X₂–CH₃ | R | cyclohexyl-X₃ | H₃C–X₄ | X₅-(N-methyl-piperidinyl) |
| 95 | H | X₂–CH₃ | R | cyclohexyl-X₃ | H₃C–X₄ | X₅-(N-methyl-8-azabicyclo) |
| 96 | H | X₂–CH₂CH₃ | R | cyclohexyl-X₃ | H₃C–O–X₄ | X₅-(N-methyl-piperidinyl) |

TABLE 1-continued

| Ex. | R¹ | R² | Config. R¹ or R² | R³ | R⁴ | Lₙ—R⁵ₘ |
|---|---|---|---|---|---|---|
| 97 | H | X₂—CH₃ (wedge) | R | X₃-cyclohexyl | H₃C-O-X₄ | X₅-cyclohexyl-N-morpholine |
| 98 | H | X₂—CH₃ (dash) | R | X₃-cyclohexyl | X₄-O-CH₃ | X₅-cyclohexyl-N-pyrrolidine |
| 99 | H | X₂—CH₃ | R | X₃-CH(CH₃)₂ | X₄-O-CH₃ | X₅-cyclohexyl-N-piperazine-N-CH₂-cyclopropyl |
| 100 | H | X₂—CH₃ (dash) | R | X₃-CH₂CH(CH₃)₂ | X₄-O-CH₃ | X₅-cyclohexyl-N-piperazine-N-CH₂-cyclopropyl |

TABLE 1-continued

| Ex. | R¹ | R² | Config. R¹ or R² | R³ | R⁴ | Lₙ—R⁵ₘ |
|---|---|---|---|---|---|---|
| 101 | H | X₂—CH₃ | R | X₃—CH(CH₃)₂ | CH₃O—X₄ | piperidine-N-benzyl (X₅) |
| 102 | H | X₂—CH₂CH₃ | R | X₃—CH(CH₃)₂ | CH₃O—X₄ | piperidine-N-benzyl (X₅) |
| 103 | H | X₂—CH₃ | R | X₃-cyclopentyl | CH₃O—X₄ | piperidine-N-benzyl (X₅) |
| 104 | H | X₂—CH₃ | R | X₃-phenyl | CH₃O—X₄ | piperidine-N-benzyl (X₅) |

TABLE 1-continued

| Ex. | R¹ | R² | Config. R¹ or R² | R³ | R⁴ | Lₙ—R⁵ₘ |
|---|---|---|---|---|---|---|
| 105 | H | X₂─CH₃ | R | X₃-cyclopentyl | X₄-O-CH₃ | X₅-cyclohexyl-piperazine-N-CH₂-cyclopropyl |
| 106 | H | X₂─CH₃ | R | X₃-cyclopentyl | X₄-O-CH₃ | X₅-cyclohexyl-piperazine-N-CH₃ |
| 107 | H | X₂─CH₃ | R | X₃-cyclopentyl | X₄-O-CH₃ | X₅-cyclohexyl-piperazine-N-CH₂-cyclopropyl |
| 108 | H | X₂─CH₂CH₃ | R | X₃-CH(CH₃)₂ | CH₃-O-X₄ | X₅-cyclohexyl-morpholine |

TABLE 1-continued

| Ex. | R¹ | R² | Config. R¹ or R² | R³ | R⁴ | Lₙ—R⁵ₘ |
|---|---|---|---|---|---|---|
| 109 | H | X₂―CH₃ | R | cyclopentyl-X₃ | CH₃-O-X₄ | X₅-cyclohexyl-morpholine |
| 110 | H | X₂―CH₂CH₃ | R | (H₃C)₂CH-X₃ | X₄-O-CH₃ | X₅-cyclohexyl-piperazine-CH₂-cyclopropyl |
| 111 | H | X₂―CH₃ | R | (H₃C)₂CHCH₂CH₂-X₃ | CH₃-O-X₄ | X₅-cyclohexyl-morpholine |
| 112 | H | X₂―CH₃ | R | (H₃C)₂CH-X₃ | X₄-O-CH₃ | X₅-cyclohexyl-piperazine-CH₂-cyclopropyl |

TABLE 1-continued

| Ex. | R¹ | R² | Config. R¹ or R² | R³ | R⁴ | L$_n$—R⁵$_m$ |
|---|---|---|---|---|---|---|
| 113 | H | X₂—CH₃ (ethyl) | R | X₃-CH(CH₃)₂ | X₄-O-CH₃ | X₅-cyclohexyl-N(piperazine)-N-CH₃ |
| 114 | H | X₂—CH₃ | R | X₃-CH₂CH(CH₃)₂ | X₄-O-CH₃ | X₅-cyclohexyl-N(CH₃)₂ |
| 115 | H | X₂—CH₃ | R | X₃-cyclohexyl | CH₃-O-X₄ | X₃-(4-piperidinyl)-N-benzyl |
| 116 | H | X₂—CH₂CH₃ | R | X₃-cyclopentyl | CH₃-O-X₄ | X₅-(4-piperidinyl)-N-(4-tetrahydropyranyl) |
| 117 | H | X₂—CH₃ | R | X₃-cyclohexyl | CH₃-O-X₄ | X₅-(2,2,6,6-tetramethyl-N-methyl-4-piperidinyl) |

TABLE 1-continued

| Ex. | R¹ | R² | Config. R¹ or R² | R³ | R⁴ | Lₙ—R⁵ₘ |
|---|---|---|---|---|---|---|
| 118 | H | X₂—CH₃ | R | X₃-cyclohexyl | CH₃-O-X₄ | 1-isopropyl-piperidin-4-yl (X₅) |
| 119 | H | X₂—CH₃ | R | X₃-cyclohexyl | CH₃-O-X₄ | 1-ethyl-piperidin-4-yl (X₅) |
| 120 | H | X₂—CH₃ | R | X₃-cyclohexyl | CH₃-O-X₄ | 1-(tetrahydropyran-4-yl)-piperidin-4-yl (X₅) |
| 121 | H | X₂—CH₃ | R | X₃-cyclohexyl | CH₃-O-X₄ | (3R)-1-ethyl-pyrrolidin-3-yl (X₅) |
| 122 | H | X₂—CH₃ | R | X₃-cyclohexyl | CH₃-O-X₄ | (3R)-1-isopropyl-pyrrolidin-3-yl (X₅) |

TABLE 1-continued

| Ex. | R¹ | R² | Config. R¹ or R² | R³ | R⁴ | Lₙ—R⁵ₘ |
|---|---|---|---|---|---|---|
| 123 | H | X₂◂CH₃ | R | X₃–cyclohexyl | CH₃–O–X₄ | X₅–(3-ethylpyrrolidin-1-yl) |
| 124 | H | X₂◂CH₃ | R | X₃–cyclohexyl | CH₃–O–X₄ | X₅–(3-isopropylpyrrolidin-1-yl) |
| 125 | H | X₂◂CH₃ | R | X₃–cyclohexyl | X₄–O–CH₃ | X₅–(4-pyrrolidin-1-yl-cyclohexyl) |
| 126 | H | X₂◂CH₃ | R | X₃–cyclohexyl | X₄–O–CH₃ | X₅–(4-piperidin-1-yl-cyclohexyl) |
| 127 | H | X₂◂CH₃ | R | X₃–cyclohexyl | X₄–O–CH₃ | X₅–(4-piperidin-1-yl-cyclohexyl) |

TABLE 1-continued

| Ex. | R¹ | R² | Config. R¹ or R² | R³ | R⁴ | Lₙ—R⁵ₘ |
|---|---|---|---|---|---|---|
| 128 | H | X₂—CH₃ | R | X₃-cyclopentyl | X₄—O—CH₃ | X₅-cyclohexyl-piperidinyl |
| 129 | H | X₂—CH₃ | R | X₃-CH(CH₃)₂ | X₄—O—CH₃ | X₅-cyclohexyl-piperidinyl |
| 130 | H | X₂—CH₃ | R | X₃-cyclohexyl | X₄—O—CH₃ | X₅-cyclohexyl-morpholinyl |
| 131 | H | X₂—CH₃ | R | X₃-cyclopentyl | X₄—O—CH₃ | X₅-cyclohexyl-morpholinyl |
| 132 | H | X₂—CH₃ | R | X₃-CH(CH₃)₂ | X₄—O—CH₃ | X₅-cyclohexyl-pyrrolidinyl |

TABLE 1-continued
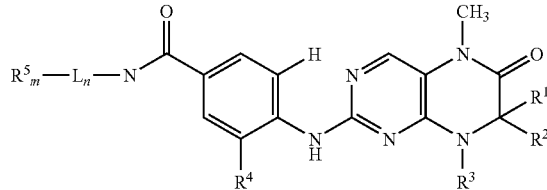

TABLE 1-continued

| Ex. | R¹ | R² | Config. R¹ or R² | R³ | R⁴ | Lₙ—R⁵ₘ |
|---|---|---|---|---|---|---|
| 137 | H | X₂⏤CH₃ | R | X₃-cyclohexyl | X₄-O-CH₃ | X₅-cyclohexyl-morpholine |
| 138 | H | X₂-CH₂CH₃ | R | X₃-cyclopentyl | X₄-O-CH₃ | X₅-cyclohexyl-pyrrolidine |
| 139 | H | X₂-CH₂CH₃ | R | X₃-CH(CH₃)₂ | H₃C-O-X₄ | X₅-N-methyl-azabicyclic |
| 140 | H | X₂-CH₂CH₃ | R | X₃-CH(CH₃)₂ | H₃C-O-X₄ | X₅-N-methylpiperidine |
| 141 | H | X₂-CH₂CH₃ | R | X₃-CH(CH₃)₂ | H₃C-O-X₄ | X₃-(CH₂)₃-morpholine |

TABLE 1-continued

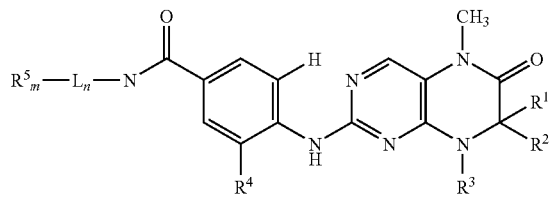

| Ex. | R¹ | R² | Config. R¹ or R² | R³ | R⁴ | Lₙ—R⁵ₘ |
|---|---|---|---|---|---|---|
| 142 | H | X₂—CH₃ | R | X₃—CH(CH₃)₂ | CH₃O—X₄ | X₃—(CH₂)₃—N-piperidine |
| 143 | H | X₂—CH₃ | R | X₃—CH(CH₃)₂ | H | X₅—(CH₂)₃—N-morpholine |
| 144 | H | X₂—CH₃ | R | X₃—CH(CH₃)₂ | H | X₅—(1-methylpiperidin-4-yl) |
| 145 | H | H₃C—X₂ | R | X₃—CH₂—C(CH₃)₂—CH₃ (neopentyl) | CH₃O—X₄ | X₅—(1-methylpiperidin-4-yl) |
| 146 | H | X₂—CH₃ | R | X₃—CH₂—CH₂—CH(CH₃)₂ | X₄—O—CH₃ | X₅—(1-methylpiperidin-4-yl) |
| 147 | H | H₃C—X₂ | R | X₃—CH₂—C(CH₃)₂—CH₃ | H | X₅—(N-methyl bicyclic amine) |
| 148 | H | X₂—CH₂—CH₃ | R | X₃—CH₂—CH₂—CH(CH₃)₂ | CH₃O—X₄ | X₅—(CH₂)₂—N-piperidine |

TABLE 1-continued

| Ex. | R¹ | R² | Config. R¹ or R² | R³ | R⁴ | Lₙ—R⁵ₘ |
|---|---|---|---|---|---|---|
| 149 | H | X₂—CH₃ (ethyl) | R | X₃—CH₂CH₂CH(CH₃)CH₃ | CH₃—O—X₄ | X₅—CH₂CH₂—N(CH₂CH₃)₂ |
| 150 | H | X₂—CH₃ (ethyl) | R | X₃—CH₂CH₂CH(CH₃)CH₃ | H | X₅—CH₂CH₂-piperidinyl |
| 151 | H | X₂—CH₃ (ethyl) | R | X₃—CH₂CH₂CH(CH₃)CH₃ | CH₃—O—X₄ | X₅—CH₂CH₂CH₂-morpholinyl |
| 152 | H | X₂—CH₃ (ethyl) | R | X₃—CH₂CH₂CH(CH₃)CH₃ | CH₃—O—X₄ | X₅—CH₂CH₂CH₂-(4-methylpiperazin-1-yl) |
| 153 | H | X₂—CH₃ (ethyl) | R | X₃—CH₂CH₂CH(CH₃)CH₃ | CH₃—O—X₄ | X₅—(CH₂)₄—N(CH₂CH₃)₂ |
| 154 | H | X₂—CH₃ (ethyl) | R | X₃—CH₂CH₂CH(CH₃)CH₃ | H | X₅—CH₂CH₂CH₂-(4-methylpiperazin-1-yl) |

TABLE 1-continued

| Ex. | R¹ | R² | Config. R¹ or R² | R³ | R⁴ | Lₙ—R⁵ₘ |
|---|---|---|---|---|---|---|
| 155 | H | X₂-CH₃ | R | X₃-CH₂CH₂-CH(CH₃)₂ | H | X₅-(CH₂)₃-morpholine |
| 156 | H | X₂-CH₃ | R | X₃-CH₂CH₂-CH(CH₃)₂ | CH₃-O-X₄ | X₅-(CH₂)₂-morpholine |
| 157 | H | X₂-CH₃ | R | X₃-CH₂CH₂-CH(CH₃)₂ | CH₃-O-X₄ | X₅-(CH₂)₃-pyrrolidine |
| 158 | H | X₂-CH₃ | R | X₃-CH₂CH₂-CH(CH₃)₂ | CH₃-O-X₄ | X₅-CH₂CH₂-N(CH₂CH₃)₂ |
| 159 | H | X₂-CH₃ | R | X₃-CH₂CH₂-CH(CH₃)₂ | CH₃-O-X₄ | X₅-CH₂CH₂-N(CH₃)₂ |
| 160 | H | X₂-CH₃ | R | X₃-CH₂CH₂-CH(CH₃)₂ | CH₃-O-X₄ | X₅-CH₂CH₂-N(CH(CH₃)₂)₂ |

TABLE 1-continued

| Ex. | R¹ | R² | Config. R¹ or R² | R³ | R⁴ | Lₙ—R⁵ₘ |
|---|---|---|---|---|---|---|
| 161 | X₁—CH₃ | X₂—CH₂CH₃ | | X₃—CH₂CH₂CH(CH₃)₂ | H₃C—O—X₄ | X₅—CH₂CH₂N(CH₂CH₃)₂ |
| 162 | X₁—CH₃ | X₂—CH₂CH₃ | | X₃—CH₂CH₂CH(CH₃)₂ | H₃C—O—X₄ | X₅—(1-methylpiperidin-4-yl) |
| 163 | H | X₂—CH₂CH₃ | R | X₃—CH₂CH₂CH(CH₃)₂ | CH₃—O—X₄ | X₅—(quinuclidin-3-yl) |
| 164 | H | X₂—CH₂CH₃ | R | X₃—CH₂CH₂CH(CH₃)₂ | CH₃—O—X₄ | X₅—CH₂CH₂CH₂N(CH₃)₂ |
| 165 | H | X₂—CH₂CH₃ | R | X₃—CH₂CH₂CH(CH₃)₂ | CH₃—O—X₄ | X₅—CH₂CH₂CH₂N(CH₂CH₃)₂ |
| 166 | H | X₁—CH₂CH₃ | R | X₃—cyclopentyl | CH₃—O—X₄ | X₅—(4-(morpholinomethyl)phenyl) |

TABLE 1-continued

| Ex. | R¹ | R² | Config. R¹ or R² | R³ | R⁴ | Lₙ—R⁵ₘ |
|---|---|---|---|---|---|---|
| 167 | H | X₂—CH₃ (wedge) | R | X₃—CH₂CH₂—CH(CH₃)₂ | CH₃—O—X₄ | X₅—CH₂CH₂-(N-methylpyrrolidin-2-yl) |
| 168 | H | X₂—CH₃ | R | X₃—CH₂CH₂—CH(CH₃)₂ | CH₃—O—X₄ | X₅—CH₂—C(CH₃)₂—CH₂—N(CH₃)₂ (with additional N(CH₃)) |
| 169 | H | X₂—CH₃ | R | X₃—CH₂CH₂—CH(CH₃)₂ | CH₃—O—X₄ | X₅—(CH₂)₃—piperidin-1-yl |
| 170 | H | X₂—CH₃ | R | X₃—CH₂CH₂—CH(CH₃)₂ | CH₃—O—X₄ | X₅—CH₂CH₂—pyrrolidin-1-yl |
| 171 | H | X₂—CH₃ | R | X₃—CH₂CH₂—CH(CH₃)₂ | CH₃—O—X₄ | X₅—(1-methylpiperidin-4-yl) |
| 172 | H | X₂—CH₃ | R | X₃—CH₂CH₂—CH(CH₃)₂ | CH₃—O—X₄ | X₅—(1-methylazepan-4-yl) |

TABLE 1-continued

| Ex. | R¹ | R² | Config. R¹ or R² | R³ | R⁴ | Lₙ—R⁵ₘ |
|---|---|---|---|---|---|---|
| 173 | H | X₂—CH₃ (wedge) | R | X₃—CH₂CH(CH₃)₂ (isobutyl-CH₂, i.e., isopentyl) | OCH₃, X₄ | X₅-N-methyl tropane (3-substituted) |
| 174 | H | X₂—CH₂CH₃ | R | X₃—CH₂CH(CH₃)₂ | OCH₃, X₄ | 1-benzylpiperidin-4-yl (X₅) |
| 175 | H | X₂—CH₃ (wedge) | R | X₃—cyclopentyl | OCH₃, X₄ | X₅—C(CH₃)₂—CH₂—N(CH₃)₂ |
| 176 | H | X₂—CH₂CH₃ | R | X₃—CH(CH₃)₂ | OCH₃, X₄ | X₅—C(CH₃)₂—CH₂—N(CH₃)₂ |
| 177 | H | X₂—CH₂CH₃ | R | X₃—cyclopentyl | OCH₃, X₄ | X₅—C(CH₃)₂—CH₂—N(CH₃)₂ |
| 178 | H | X₂—CH₂CH₃ | R | X₃—CH(CH₃)₂ | OCH₃, X₄ | piperidin-4-yl (X₅) |
| 179 | H | X₂—CH₂CH₃ | R | X₃—CH₂CH(CH₃)₂ | OCH₃, X₄ | piperidin-4-yl (X₅) |

TABLE 1-continued

| Ex. | R¹ | R² | Config. R¹ or R² | R³ | R⁴ | Lₙ—R⁵ₘ |
|---|---|---|---|---|---|---|
| 180 | H | X₂—CH₃ | R | X₃-cyclohexyl | H₃C-O-X₄ | X₅-(1-benzylpiperidin-4-yl) |
| 181 | H | X₂◂CH₃ | R | X₃-tetrahydropyran-4-yl | CH₃-O-X₄ | X₃-(1-benzylpiperidin-4-yl) |
| 182 | H | X₂◂CH₃ | R | X₃-cyclopentyl | CH₃-O-X₄ | H₃C-C(CH₃)₂-CH₂-morpholino, X₅ |
| 183 | H | X₂—CH₃ | R | X₃-isopropyl | CH₃-O-X₄ | H₃C-C(CH₃)₂-CH₂-morpholino, X₅ |
| 184 | H | X₂—CH₃ | R | X₃-cyclopentyl | CH₃-O-X₄ | H₃C-C(CH₃)₂-CH₂-morpholino, X₅ |

TABLE 1-continued

| Ex. | R¹ | R² | Config. R¹ or R² | R³ | R⁴ | Lₙ—R⁵ₘ |
|---|---|---|---|---|---|---|
| 185 | H | X₂—CH₃ | R | X₃—(4-methoxyphenyl) | CH₃O—X₄ | X₅—CH₂C(CH₃)₂—morpholine |
| 186 | H | X₂—CH₃ | R | X₃—cyclohexyl | CH₃O—X₄ | X₅—(4-(4-methylpiperazin-1-yl)phenyl) |
| 187 | H | X₂—CH₂CH₃ | R | X₃—cyclopentyl | CH₃O—X₄ | X₅—(4-(4-methylpiperazin-1-yl)phenyl) |
| 188 | H | X₂—CH₃ | R | X₃—cyclopentyl | Cl—X₄ | X₅—(4-methylpiperazin-1-yl) |

TABLE 1-continued

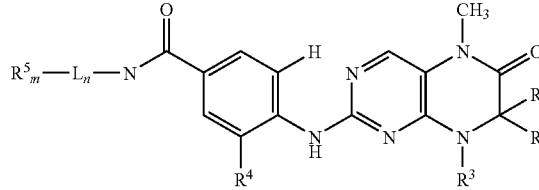

| Ex. | R¹ | R² | Config. R¹ or R² | R³ | R⁴ | L$_n$—R$^5_m$ |
|---|---|---|---|---|---|---|
| 189 | H | X₂—CH₃ | R | X₃-cyclohexyl | X₄—O—CH₃ | X₅-cyclohexyl-morpholine (trans) |
| 190 | H | X₂◂CH₃ | R | X₃-cyclopentyl | CH₃—O—X₄ | X₅-piperidine |
| 191 | H | X₂-cyclopropyl | R | X₃-isopropyl | H₃C-CH₂-O-X₄ | X₅-N-methylpiperidine |
| 192 | H | X₂◂CH₃ | R | X₃-cyclohexyl | CH₃—O—X₄ | X₅-C(CH₃)₂-CH₂-morpholine |
| 193 | H | X₂—CH₃ | R | X₃-cyclohexyl | CH₃—O—X₄ | X₅-C(CH₃)₂-CH₂-morpholine |
| 194 | H | X₂—CH₃ | R | X₃-phenyl | CH₃—O—X₄ | X₅-C(CH₃)₂-CH₂-morpholine |

TABLE 1-continued
| Ex. | R¹ | R² | Config. R¹ or R² | R³ | R⁴ | Lₙ—R⁵ₘ |
|-----|----|----|------------------|----|----|--------|
| 195 | H | 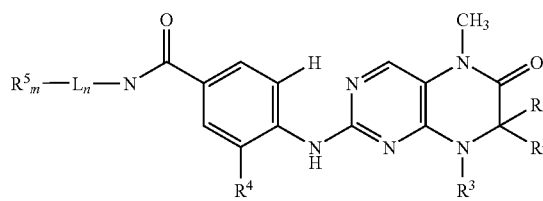 | R |  | 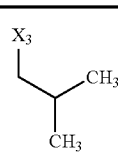 | 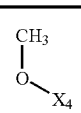 |
| 196 | H |  | R | 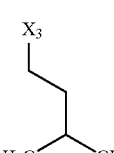 | 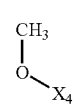 |  |
| 197 | H | 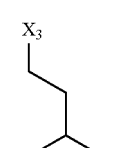 | | 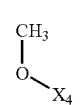 |  |  |
| 198 | H |  | R | |  | 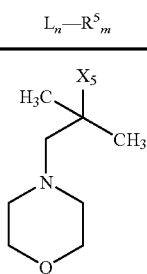 |
| 199 | H | | R | | | |

TABLE 1-continued
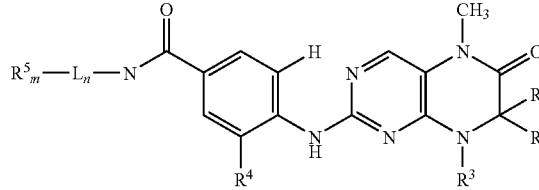
| Ex. | R¹ | R² | Config. R¹ or R² | R³ | R⁴ | Lₙ—R⁵ₘ |
|---|---|---|---|---|---|---|
| 200 | H |  | R | |  | 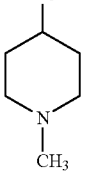 |
| 201 | H |  | R | |  | 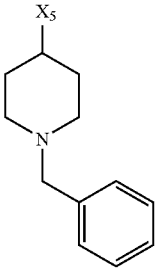 |
| 202 |  |  | | 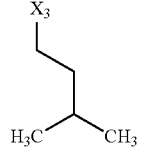 |  | 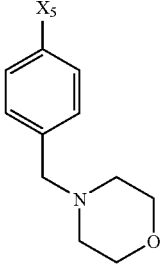 |
| 203 | H |  | R | 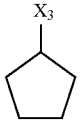 |  |  |
| 204 | H | 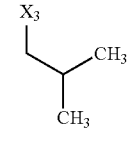 | R |  | | |

TABLE 1-continued

| Ex. | R¹ | R² | Config. R¹ or R² | R³ | R⁴ | Lₙ—R⁵ₘ |
|---|---|---|---|---|---|---|
| 205 | H | X₂◂CH₃ | R | X₃ isobutyl | X₄—O—CH₃ | X₅-cyclohexyl-morpholine |
| 206 | H | X₂◂CH₃ | R | X₃ neopentyl | X₄—O—CH₃ | X₅-cyclohexyl-piperazine-CH₂-cyclopropyl |
| 207 | H | X₂◂CH₃ | R | X₃ neopentyl | X₄—O—CH₃ | X₅-cyclohexyl-morpholine |
| 208 | H | X₂◂CH₃ | R | X₃ neopentyl | X₄—O—CH₃ | X₅-cyclohexyl-piperazine-CH₂-cyclopropyl |

TABLE 1-continued

| Ex. | R¹ | R² | Config. R¹ or R² | R³ | R⁴ | Lₙ—R⁵ₘ |
|---|---|---|---|---|---|---|
| 209 | H | X₂—CH₃ | R | X₃—CH(CH₃)₂ | X₄—O—CH₃ | X₅-cyclohexyl-N-piperazine-N-CH₃ |
| 210 | H | X₂—CH₃ | R | X₃-cyclopentyl | X₄—O—CH₃ | X₅-cyclohexyl-N-piperazine-N-CH₃ |
| 211 | X₁—CH₃ | X₂—CH₃ | | X₃—CH₂CH₂CH(CH₃)₂ | X₄—O—CH₃ | X₅-cyclohexyl-morpholine |
| 212 | X₁—CH₃ | X₂—CH₃ | | X₃—CH₂CH₂CH(CH₃)₂ | X₄—O—CH₃ | X₅-cyclohexyl-N-piperazine-N-CH₂-cyclopropyl |

TABLE 1-continued
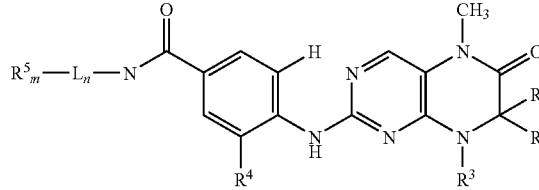
| Ex. | R¹ | R² | Config. R¹ or R² | R³ | R⁴ | L$_n$—R⁵$_m$ |
|---|---|---|---|---|---|---|
| 213 | H | X$_2$—CH$_3$ | R | X$_3$-cyclohexyl | X$_4$—O—CH$_3$ | X$_5$-cyclohexyl-N(piperazine)-N-C(O)CH$_3$ |
| 214 | H | X$_2$—CH$_2$—CH$_3$ | R | X$_3$—CH(CH$_3$)$_2$ | X$_4$—O—CH$_3$ | X$_5$-cyclohexyl-N(piperazine)-N-CH$_3$ |
| 215 | X$_1$—CH$_3$ | X$_2$—CH$_3$ | | X$_3$—CH$_2$CH$_2$CH(CH$_3$)$_2$ | X$_4$—O—CH$_3$ | X$_5$-cyclohexyl-N(piperazine)-N-CH$_3$ |
| 216 | H | X$_2$—CH$_3$ | R | X$_3$-cyclohexyl | X$_4$—O—CH$_3$ | X$_5$-cyclohexyl-N(piperazine)-N-CH$_3$ |

TABLE 1-continued

| Ex. | R¹ | R² | Config. R¹ or R² | R³ | R⁴ | Lₙ—R⁵ₘ |
|---|---|---|---|---|---|---|
| 217 | H | X₂—CH₃ | R | X₃-cyclopentyl | X₄-O-CH₃ | X₅-cyclohexyl-N(piperazine)-N-CH₃ |
| 218 | H | X₂—CH₃ | R | X₃-CH₂CH(CH₃)₂ (isopentyl) | X₄-O-CH₃ | X₅-cyclohexyl-N(thiomorpholine) |
| 219 | H | X₂—CH₃ | R | X₃-CH₂CH(CH₃)₂ (isopentyl) | X₄-O-CH₃ | X₅-cyclohexyl-N(morpholine) |
| 220 | H | X₂—CH₃ | R | X₃-CH₂C(CH₃)₃ (neopentyl) | X₄-O-CH₃ | X₅-cyclohexyl-N(morpholine) |

TABLE 1-continued

| Ex. | R¹ | R² | Config. R¹ or R² | R³ | R⁴ | Lₙ—R⁵ₘ |
|---|---|---|---|---|---|---|
| 221 | H | X₂⫸CH₃ | R | X₃–CH₂CH₂–CH(CH₃)₂ | X₄–O–CH₃ | X₅–(trans-cyclohexyl)–N(piperazine)–N–CH₃ |
| 222 | H | X₂–CH₂CH₃ | R | X₃–CH₂CH₂–CH(CH₃)₂ | X₄–O–CH₃ | X₅–(trans-cyclohexyl)–N(piperazine)–N–CH₃ |
| 223 | H | X₂⫸CH₃ | R | X₃–phenyl | X₄–OCH₂CH₃ | X₅–(4-piperidinyl)–N–CH₃ |
| 224 | H | X₂⫸CH₃ | R | X₃–(3-methoxyphenyl) | X₄–O–CH₃ | X₅–(4-piperidinyl)–N–CH₃ |
| 225 | H | X₂⫸CH₃ | R | X₃–(3-methoxyphenyl) | H | X₅–(4-piperidinyl)–N–CH₃ |

TABLE 1-continued

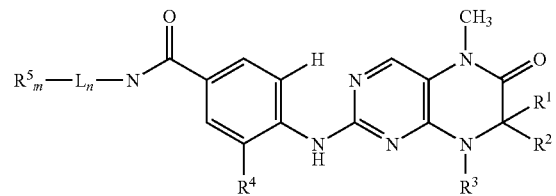

| Ex. | R¹ | R² | Config. R¹ or R² | R³ | R⁴ | Lₙ—R⁵ₘ |
|---|---|---|---|---|---|---|
| 226 | H | X₂▬CH₃ | R | X₃-(2-methoxyphenyl) | H₃C-O-X₄ | X₅-(1-methylpiperidin-4-yl) |
| 227 | H | X₂▬CH₃ | R | X₃-(2-methoxyphenyl) | CH₃-O-X₄ | H₃C-C(CH₃)(X₅)-CH₂-pyrrolidin-1-yl |
| 228 | H | X₂▬CH₃ | R | X₃-CH₂CH₂CH(CH₃)₂ | X₄-O-CH₃ | X₅-trans-cyclohexyl-(4-methylpiperazin-1-yl) |
| 229 | H | X₂—CH₃ | R | X₃-phenyl | CH₃-O-X₄ | H₃C-C(CH₃)(X₅)-CH₂-piperidin-1-yl |
| 230 | H | X₂▬CH₃ | R | X₃-cyclohexyl | CH₃-O-X₄ | H₃C-C(CH₃)(X₅)-CH₂-piperidin-1-yl |
| 231 | H | X₂—CH₃ | R | X₃-cyclopentyl | CH₃-O-X₄ | H₃C-C(CH₃)(X₅)-CH₂-piperidin-1-yl |

TABLE 1-continued

| Ex. | R¹ | R² | Config. R¹ or R² | R³ | R⁴ | Lₙ—R⁵ₘ |
|---|---|---|---|---|---|---|
| 232 | H | X₂—CH₃ | R | X₃—cyclohexyl | X₄—O—CH₃ | X₅—cyclohexyl-piperazinyl |
| 233 | H | X₁—CH₃ | R | X₃—CH₂C(CH₃)₃ | X₄—O—CH₃ | X₅—cyclohexyl-(2,6-dimethylmorpholinyl) |
| 234 | H | X₁—CH₃ (with ethyl) | R | X₃—CH(CH₃)₂ | X₄—O—CH₃ | X₅—cyclohexyl-(2,6-dimethylmorpholinyl) |
| 235 | H | X₁—CH₃ | R | X₃—CH₂CH(CH₃)₂ | X₄—O—CH₃ | X₅—cyclohexyl-(thiomorpholine S-oxide) |

TABLE 1-continued

| Ex. | R¹ | R² | Config. R¹ or R² | R³ | R⁴ | Lₙ—R⁵ₘ |
|---|---|---|---|---|---|---|
| 236 | H | X₁―CH₃ | R | X₃―CH(CH₂)CH(CH₃)CH₃ | X₄―O―CH₃ | X₅-cyclohexyl-N-thiomorpholine S-oxide |
| 237 | H | X₁―CH₂CH₃ | R | X₃―CH(CH₃)₂ | CH₃―O―X₄ | X₅-piperidin-4-yl |
| 238 | H | X₁―CH₃ | R | X₃-cyclopentyl | CH₃―O―X₄ | X₅-piperidin-4-yl |
| 239 | H | X₁―CH₂CH₃ | R | X₃-cyclopentyl | CH₃―O―X₄ | H₃C-C(X₅)(CH₃)-CH₂-morpholine |
| 240 | H | X₁―CH₃ | R | X₃-cyclohexyl | CH₃―O―X₄ | H₃C-C(X₅)(CH₃)-CH₂-N(CH₃)₂ |

TABLE 1-continued

| Ex. | R¹ | R² | Config. R¹ or R² | R³ | R⁴ | Lₙ—R⁵ₘ |
|---|---|---|---|---|---|---|
| 241 | H | X₁⁀CH₃ | R | X₃-CH₂CH₂-CH(CH₃)₂ | CH₃-O-X₄ | H₃C-C(CH₃)(X₅)-CH₂-N(piperazine)-N-CH₃ |
| 242 | H | X₁⁀CH₃ | R | X₃-CH₂CH₂-CH(CH₃)₂ | CH₃-O-X₄ | X₅-CH₂CH₂-N(piperidine) |
| 243 | H | X₁⁀CH₃ | R | X₃-CH₂CH₂-CH(CH₃)₂ | CH₃-O-X₄ | X₅-CH₂CH₂CH₂-N(CH₃)₂ |
| 244 | H | X₁⁀CH₃ | R | X₃-CH₂CH₂-CH(CH₃)₂ | CH₃-O-X₄ | X₅-CH₂CH₂CH₂-N(piperazine)-N-CH₃ |

What is claimed:

1. A Storage stable aqueous infusible or injectable solution containing an active substance of general formula (I)

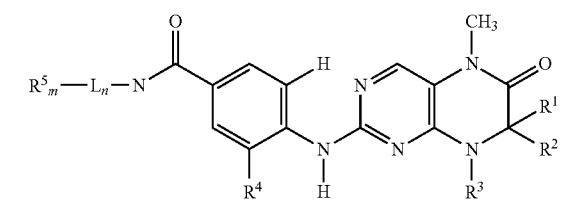

| Ex. | $R^1$ | $R^2$ | Config. $R^1$ or $R^2$ | $R^3$ | $R^4$ | $L_n$—$R^5_m$ |
|---|---|---|---|---|---|---|
| 110 | H | 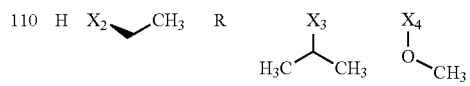 | R | 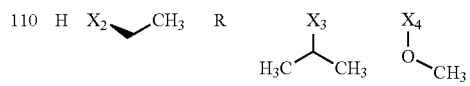 | 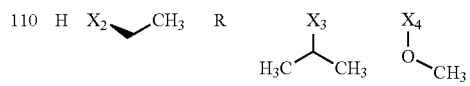 | 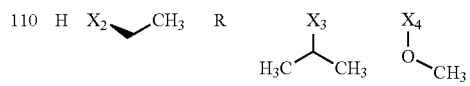 |
| 46 | H | 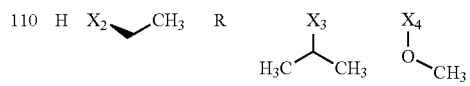 | R | 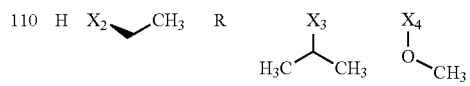 | 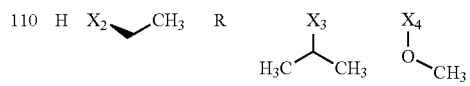 | 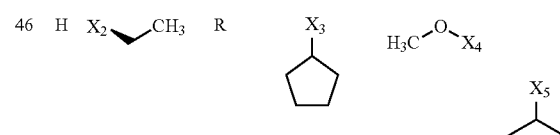 | whereby the abbreviations $X_1$, $X_2$, $X_3$, $X_4$ and $X_5$ used in the Table in each case denote a link to a position in the general formula listed in the Table instead of the corresponding groups $R^1$, $R^2$, $R^3$, $R^4$ and L-$R^5$ or the tautomers, racemates, enantiomers or diastereomers and an amount of a physiologically acceptable acid or mixture of acids wherein the solution has a pH of 2.4 to 5.3 optionally together with other formulating excipients suitable for parenteral administration.

2. The solution according to claim 1 wherein the active substance of general formula (I)

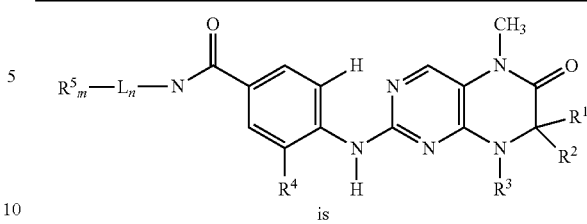

is

| Ex. | $R^1$ | $R^2$ | Config. $R^1$ or $R^2$ | $R^3$ | $R^4$ | $L_n$—$R^5_m$ |
|---|---|---|---|---|---|---|
| 110 | H | 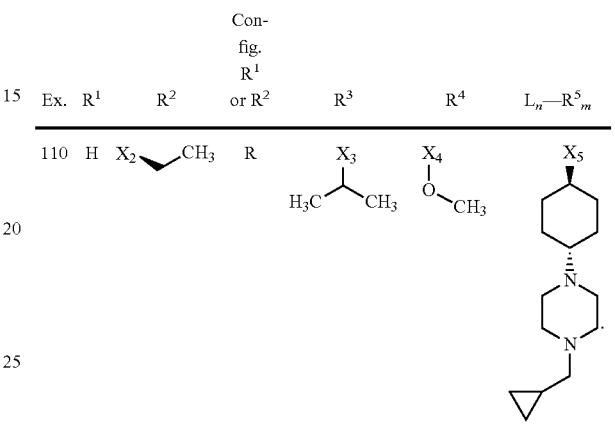 | R | 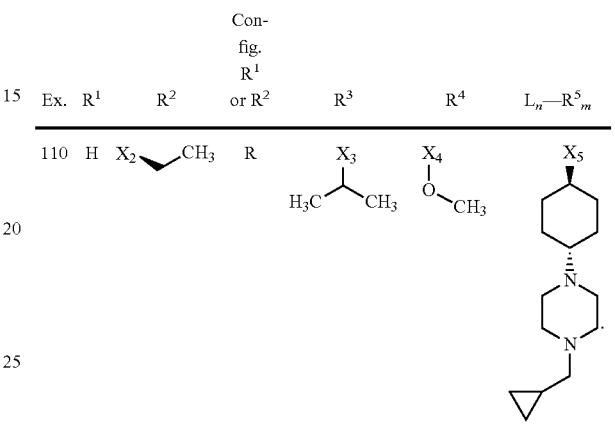 | 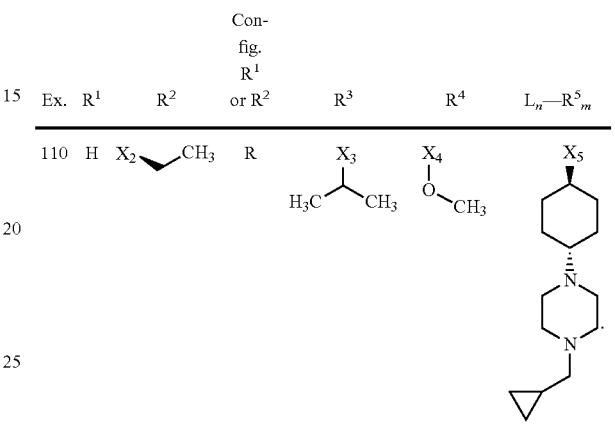 | 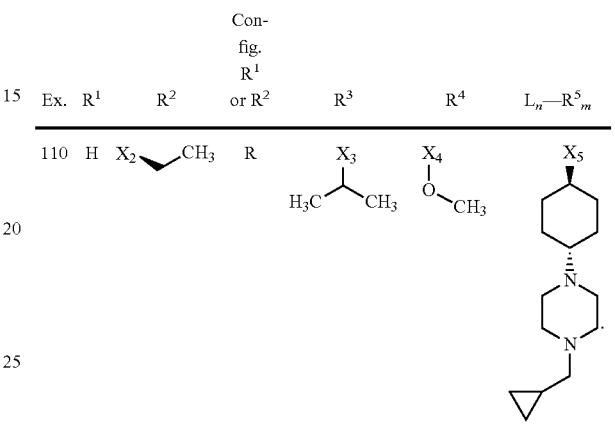 |

3. The solution according to claim 2, wherein the content of dissolved active substance is 0.1 mg to 10.0 mg in 1 ml of infusible or injectable solution.

4. The solution according to claim 3, wherein one or more acids used as storage and dilution stabilisers are selected from hydrochloric acid, acetic acid, hydroxyacetic acid, methanesulphonic acid, ethanesulphonic acid, phosphoric acid, nitric acid, sulphuric acid, citric acid, tartaric acid, fumaric acid, succinic acid, glutaric acid, adipic acid, propionic acid, ascorbic acid, maleic acid, malic acid, glutamic acid, gluconic acid, glucuronic acid, galacturonic acid and lactic acid.

5. The solution according to claim 4, wherein it contains one or more other formulating excipients selected from among complexing agents, light protecting agents, crystallisation inhibitors, thickeners, isotonic agents, antioxidants and euhydration agents.

6. The solution according to claim 5, wherein the osmolality of the infusible or injectable solutions is 200-600 mOsmol/kg.

7. The solution according to claim 6, wherein it contains 1.25 to 3.0 mol hydrochloric acid per mol active substance, based on 100 ml infusible or injectable solution 0.75 to 1.2 g NaCl, and have an osmolality of 260 to 350 mOsmol/kg and a pH of 3.5 to 5.0.

8. A lyophilisate, concentrate or suspension, wherein by the addition of water they yield an aqueous infusible or injectable solution according to claim 7.

9. The solution according to claim 5 wherein the complexing agent is EDTA.

10. A glass container or flexible plastic container suitable for parenteral preparations, containing infusible or injectable solutions according to claim 1.

11. The solution according to claim 1 wherein the active substance of general formula (I)

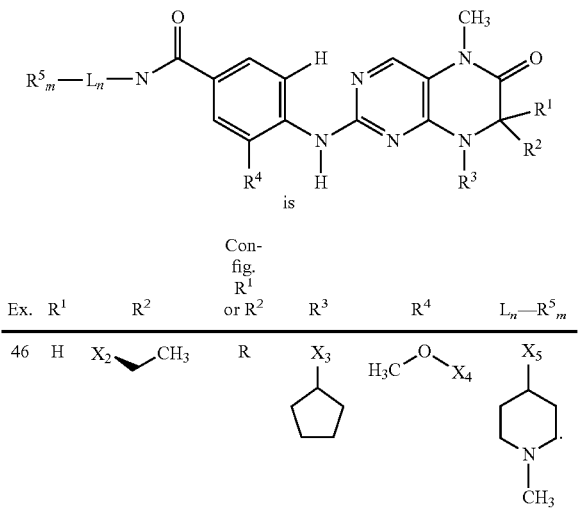

12. The solution according to claim 11, wherein the content of dissolved active substance is 0.1 mg to 10.0 mg in 1 ml of infusible or injectable solution.

13. The solution according to claim 12, wherein one or more acids used as storage and dilution stabilisers are selected from hydrochloric acid, acetic acid, hydroxyacetic acid, methanesulphonic acid, ethanesulphonic acid, phosphoric acid, nitric acid, sulphuric acid, citric acid, tartaric acid, fumaric acid, succinic acid, glutaric acid, adipic acid, propionic acid, ascorbic acid, maleic acid, malic acid, glutamic acid, gluconic acid, glucuronic acid, galacturonic acid and lactic acid.

14. The solution according to claim 13, wherein it contains one or more other formulating excipients selected from among complexing agents, light protecting agents, crystallisation inhibitors, thickeners, isotonic agents, antioxidants and euhydration agents.

15. The solution according to claim 14, wherein the osmolality of the infusible or injectable solutions is 200-600 mOsmol/kg.

16. The solution according to claim 15, wherein it contains 1.25 to 3.0 mol hydrochloric acid per mol active substance, based on 100 ml infusible or injectable solution 0.75 to 1.2 g NaCl, and have an osmolality of 260 to 350 mOsmol/kg and a pH of 3.5 to 5.0.

17. A lyophilisate, concentrate or suspension, wherein by the addition of water they yield an aqueous infusible or injectable solution according to claim 16.

18. The solution according to claim 14 wherein the complexing agent is EDTA.

* * * * *